(12) United States Patent
Ito et al.

(10) Patent No.: US 11,702,679 B2
(45) Date of Patent: Jul. 18, 2023

(54) MUTANT GENE ASSOCIATED WITH IMPROVEMENT IN ETHANOL PRODUCTIVITY VIA ETHANOL FERMENTATION AND METHOD FOR PRODUCING ETHANOL USING THE SAME

(71) Applicant: TOYOTA JIDOSHA KABUSHIKI KAISHA, Toyota (JP)

(72) Inventors: Junji Ito, Nisshin (JP); Toru Onishi, Toyota (JP); Nobuki Tada, Nisshin (JP); Rie Hirao, Handa (JP)

(73) Assignee: TOYOTA JIDOSHA KABISHIKI KAISHA, Toyota (JP)

( * ) Notice: Subject to any disclaimer, the term of this patent is extended or adjusted under 35 U.S.C. 154(b) by 59 days.

(21) Appl. No.: 17/388,338

(22) Filed: Jul. 29, 2021

(65) Prior Publication Data
US 2021/0363552 A1    Nov. 25, 2021

Related U.S. Application Data

(62) Division of application No. 16/761,676, filed as application No. PCT/JP2018/041038 on Nov. 5, 2018, now Pat. No. 11,299,757.

(30) Foreign Application Priority Data

Nov. 6, 2017   (JP) ................. 2017-214102

(51) Int. Cl.
| | | |
|---|---|---|
| *C12P 7/06* | (2006.01) | |
| *C07K 14/39* | (2006.01) | |
| *C12N 9/12* | (2006.01) | |

(52) U.S. Cl.
CPC ............... *C12P 7/06* (2013.01); *C07K 14/39* (2013.01); *C12N 9/12* (2013.01)

(58) Field of Classification Search
CPC .. C12P 7/06; C07K 14/39; C12N 9/12; Y02E 50/10
See application file for complete search history.

(56) References Cited

U.S. PATENT DOCUMENTS

| | | |
|---|---|---|
| 8,445,243 B2 | 5/2013 | Matsushika et al. |
| 8,652,817 B2 | 2/2014 | Wood et al. |
| 8,772,012 B2 | 7/2014 | Katahira et al. |
| 2011/0027847 A1 | 2/2011 | Matsushika et al. |
| 2016/0002674 A1 | 1/2016 | Onishi et al. |

FOREIGN PATENT DOCUMENTS

| | | |
|---|---|---|
| JP | 2002-238582 A | 8/2002 |
| JP | 2009-500035 A | 1/2009 |
| JP | 2009-195220 A | 9/2009 |
| JP | 2011-147445 A | 8/2011 |
| JP | 2014-193152 A | 10/2014 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Notice of Allowance, dated Dec. 21, 2021, issued by the United States Patent and Trademark Office in U.S. Appl. No. 16/761,676.
International Search Report for PCT/JP2018/041038 dated Jan. 29, 2019.
Written Opinion for PCT/JP2018/041038 dated Jan. 29, 2019.
Restriction Requirement, dated Apr. 13, 2021, issued by the United States Patent and Trademark Office in U.S. Appl. No. 16/761,676.
Non-Final Office Action, dated Jul. 16, 2021, issued by the United States Patent and Trademark Office in U.S. Appl. No. 16/761,676.
U.S. Appl. No. 16/761,676, filed May 5, 2020 (Ito et al.).
Stephanie Anne Davis Lopez., Improving *Saccharomyces cerevisiae* as a biofuel production organism. PhD Dissertation, Univ., of California, Berkeley, USA, 2015, pp. 1-117. (Year: 2015) (125 pages total).
Communication dated Dec. 9, 2022, issued in U.S. Appl. No. 17/388,280.
Stephanie Anne Davis Lopez., Improving *Saccharomyces cerevisiae* as a biofuel production organism. PhD Dissertation, Univ., of California, Berkeley, USA, 2015, pp. 1-125. (Year: 2015).

* cited by examiner

*Primary Examiner* — Ganapathirama Raghu
(74) *Attorney, Agent, or Firm* — Sughrue Mion, PLLC

(57) ABSTRACT

This invention is intended to improve the ethanol fermentation ability of a yeast strain having xylose-metabolizing ability with the use of a mutant gene encoding a mutant protein comprising a consensus sequence comprising a substitution of amino acid in the 30th position in SEQ ID NO: 1, amino acid in the 43rd position in SEQ ID NO: 4, and amino acid in the 31st position in SEQ ID NO: 7 with other amino acid residues.

4 Claims, 1 Drawing Sheet
Specification includes a Sequence Listing.

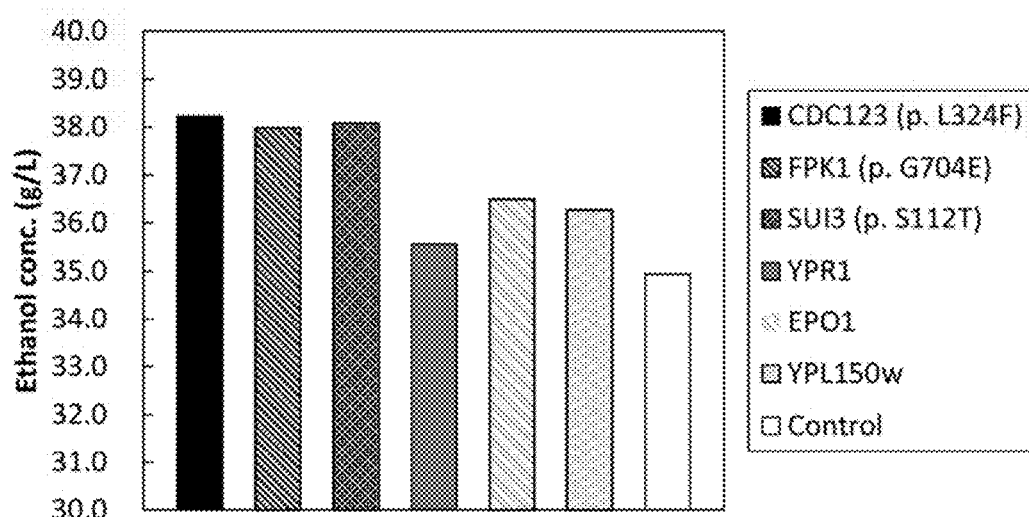

MUTANT GENE ASSOCIATED WITH IMPROVEMENT IN ETHANOL PRODUCTIVITY VIA ETHANOL FERMENTATION AND METHOD FOR PRODUCING ETHANOL USING THE SAME

CROSS REFERENCE TO RELATED APPLICATIONS

This application is a divisional of U.S. application Ser. No. 16/761,676, filed May 5, 2020, which is a National Stage of International Application No. PCT/JP2018/041038 filed Nov. 5, 2018, which claims the benefit of priority based on Japanese Patent Application No. 2017-214102 filed Nov. 6, 2017, the entire contents of which are incorporated herein by reference.

TECHNICAL FIELD

The present invention relates to a mutant gene associated with improvement in ethanol productivity in ethanol fermentation performed with a yeast strain or so on having xylose-metabolizing ability and a method for producing ethanol using the same.

BACKGROUND ART

A cellulosic biomass is an effective starting material for a useful alcohol, such as ethanol, or an organic acid. In order to increase the amount of ethanol produced with the use of a cellulosic biomass, yeast strains capable of utilizing xylose, which is pentose, as a substrate have been developed. For example, Patent Document 1 discloses a recombinant yeast strain resulting from integration of a xylose reductase (XR) gene and a xylitol dehydrogenase (XDH) gene derived from *Pichia stipitis* into its chromosome. Also, a report has been made concerning a xylose-assimilating yeast strain into which a xylose isomerase (XI) gene derived from the intestinal protozoa of *Reticulitermes speratus* has been introduced (Patent Document 2).

An attempt for improving ethanol productivity of a xylose-assimilating yeast strain or a general yeast strain that produces ethanol from glucose via fermentation has been reported. For example, Patent Document 3 reports that the alcohol-producing capacity of sake yeast strain is improved upon introduction of a particular mutation into the PDR3 gene. Also, Patent Document 4 discloses a recombinant *Klebsiella oxytoca*, which is prepared by introducing alcohol dehydrogenase and pyruvate decarboxylase into a host and deleting a gene associated with production of butanediol or 2,3-butanediol therefrom. With the use of the recombinant disclosed in Patent Document 4, ethanol can be produced with high efficiency by converting a sugar-containing substrate in a medium mainly into ethanol and decreasing conversion thereof into butanediol or 2,3-butanediol.

Patent Document 5 discloses that a recombinant yeast strain comprising a xylose metabolism-associated expression cassette introduced thereinto is subjected to acclimatization to improve the xylose fermentation ability of the recombinant yeast strain. In addition, Patent Document 6 discloses a xylose isomerase gene derived from the intestinal protozoa of *Reticulitermes speratus* or the intestinal protozoa of *Mastotermes darwiniensis*. The xylose isomerase gene disclosed in Patent Document 6 effectively functions in yeast and it is capable of improving xylose-metabolizing ability of yeast.

PRIOR ART DOCUMENTS

Patent Documents

[Patent Document 1] JP 2009-195220 A
[Patent Document 2] JP 2011-147445 A
[Patent Document 3] JP 2002-238582 A
[Patent Document 4] JP 2009-500035 A
[Patent Document 5] JP 2009-195220 A
[Patent Document 6] JP 2009-195220 A

SUMMARY OF THE INVENTION

Objects to be Attained by the Invention

Yeast strains having xylose-metabolizing ability were insufficient in terms of ethanol productivity from xylose in a medium. Under the circumstances described above, accordingly, the present invention is intended to improve ethanol fermentation ability of a yeast strain having xylose-metabolizing ability.

Means for Attaining the Objects

The present inventors have conducted concentrated studies in order to attain the above objects. As a result, they succeeded in obtaining a yeast strain with improved fermentation performance when subjecting a yeast strain with xylose-metabolizing ability to long-term continuous culture and identifying a plurality of mutations associated with excellent ethanol fermentation ability of the yeast strain via thorough analysis of the obtained strain. This has led to the completion of the present invention.

The present invention includes the following.
(1) A mutant gene encoding the mutant CDC123 protein comprising a consensus sequence comprising a substitution of an amino acid residue in the 30th position from the N terminus with another amino acid residue in SEQ ID NO: 1.
(2) The mutant gene according to (1), wherein the amino acid residue in the 30th position is any of leucine, valine, and isoleucine and the another amino acid residue is cysteine.
(3) The mutant gene according to (1), wherein the mutant CDC123 protein comprises:
   (a) the amino acid sequence as shown in SEQ ID NO: 3; or
   (b) an amino acid sequence having 70% or higher identity to the amino acid sequence of SEQ ID NO: 3 in which an amino acid residue corresponding to the 324th position from the N terminus of the amino acid sequence of SEQ ID NO: 3 is cysteine.
(4) A mutant gene encoding the SUI3 protein comprising a consensus sequence comprising a substitution of an amino acid residue in the 52nd position from the N terminus with another amino acid residue in SEQ ID NO: 4.
(5) The mutant gene according to (4), wherein the amino acid residue in the 52nd position is serine or asparagine and the another amino acid residue is threonine.
(6) The mutant gene according to (4), wherein the mutant SUI3 protein comprises:
   (a) the amino acid sequence as shown in SEQ ID NO: 6; or
   (b) an amino acid sequence having 70% or higher identity to the amino acid sequence of SEQ ID NO: 6 in which an amino acid residue corresponding to the 112th position from the N terminus of the amino acid sequence of SEQ ID NO: 6 is threonine.

(7) A mutant gene encoding the mutant FPK1 protein comprising a consensus sequence comprising a substitution of an amino acid residue in the 31st position from the N terminus with another amino acid residue in SEQ ID NO: 7.
(8) The mutant gene according to (7), wherein the amino acid residue in the 31st position is glycine and the another amino acid residue is glutamic acid.
(9) The mutant gene according to (7), wherein the mutant FPK1 protein comprises:
 (a) the amino acid sequence as shown in SEQ ID NO: 9; or
 (b) an amino acid sequence having 70% or higher identity to the amino acid sequence of SEQ ID NO: 9 in which an amino acid residue corresponding to the 704th position from the N terminus of the amino acid sequence of SEQ ID NO: 9 is glutamic acid.
(10) A mutant yeast strain having xylose-metabolizing ability, which comprises the mutant gene according to any of (1) to (9).
(11) A method for producing ethanol comprising a step of culturing the mutant yeast strain according to (10) in a xylose-containing medium and performing ethanol fermentation.
(12) The method for producing ethanol according to (11), wherein the medium contains cellulose and the ethanol fermentation proceeds simultaneously at least with the cellulose saccharification.

This description includes part or all of the content as disclosed in the description and/or drawings of Japanese Patent Application No. 2017-214102, which is a priority document of the present application.

Effects of the Invention

The mutant gene according to the present invention is capable of imparting a yeast strain having xylose-metabolizing ability with excellent ethanol fermentation ability. Specifically, the mutant yeast strain according to the present invention can exhibit excellent ethanol fermentation ability. Accordingly, the mutant gene according to the present invention, a mutant yeast strain comprising such mutant gene, and a method for producing ethanol using the same can provide excellent ethanol productivity.

BRIEF DESCRIPTION OF THE DRAWINGS

FIG. 1 shows a characteristic diagram demonstrating the results of evaluation of the ethanol fermentation ability of 6 types of mutant yeast strains each having xylose-metabolizing ability resulting from independent introduction of 6 types of mutant genes identified in the examples.

EMBODIMENTS OF THE INVENTION

Hereafter, the present invention is described in greater detail with reference to the drawing and the examples.
The mutant gene according to the present invention was identified in a mutant strain having excellent ethanol fermentation ability, which was obtained by long-term continuous culture of a recombinant yeast strain having xylose-metabolizing ability. As described in the examples below, specific 3 different mutant genes were identified. These 3 mutant genes are occasionally referred to as mutant genes 1 to 3 for convenience.
<Mutant Gene 1>
The mutant gene 1 encodes the mutant CDC123 protein comprising a substitution of a particular amino acid residue of the cell division cycle (CDC) 123 protein with another amino acid residue. CDC123 is an eIF2 translation initiation factor complex-associated factor (also referred to as an aggregation factor, architectural factor, or assembly factor) and it has a function of regulating initiation of translation. A systematic name of the gene encoding CDC123 is YLR215C.

The mutant CDC123 protein comprises a substitution mutation of a particular amino acid residue on the C-terminal side of the D123 domain. A region having such mutation is conserved among many CDC123 proteins derived from different organism species. SEQ ID NO: 1 shows the conserved region within the D123 domain comprising such mutation (i.e., a consensus sequence). The mutant CDC123 protein is defined to comprise an amino acid sequence comprising a substitution of an amino acid residue in the 30th position from the N terminus in SEQ ID NO: 1 with another amino acid residue.

The conserved region comprising the amino acid sequence as shown in SEQ ID NO: 1 is defined to be a region of 34 amino acid residues from the N terminus (the left end) in the amino acid sequences shown in the Table 1 below (lines 2 to 13). An amino acid residue indicated as Xaa at position 1 in the amino acid sequence as shown in SEQ ID NO: 1 is glutamic acid, arginine, glutamine, lycine, or aspartic acid. An amino acid residue indicated as Xaa at position 5 in the amino acid sequence as shown in SEQ ID NO: 1 is leucine or phenylalanine. An amino acid residue indicated as Xaa at position 7 in the amino acid sequence as shown in SEQ ID NO: 1 is leucine or isoleucine. An amino acid residue indicated as Xaa at position 8 in the amino acid sequence as shown in SEQ ID NO: 1 is valine, isoleucine, or leucine. An amino acid residue indicated as Xaa at position 9 in the amino acid sequence as shown in SEQ ID NO: 1 is threonine, lycine, proline, or leucine. An amino acid residue indicated as Xaa at position 10 in the amino acid sequence as shown in SEQ ID NO: 1 is arginine, serine, or glutamic acid. An amino acid residue indicated as Xaa at position 11 in the amino acid sequence as shown in SEQ ID NO: 1 is histidine, asparagine, or threonine. An amino acid residue indicated as Xaa at position 13 in the amino acid sequence as shown in SEQ ID NO: 1 is threonine, isoleucine, or valine. An amino acid residue indicated as Xaa at position 14 in the amino acid sequence as shown in SEQ ID NO: 1 is glycine, cysteine, or alanine. An amino acid residue indicated as Xaa at position 17 in the amino acid sequence as shown in SEQ ID NO: 1 is alanine or valine. An amino acid residue indicated as Xaa at position 18 in the amino acid sequence as shown in SEQ ID NO: 1 is serine, threonine, histidine, or cysteine. An amino acid residue indicated as Xaa at position 23 in the amino acid sequence as shown in SEQ ID NO: 1 is glutamic acid or glutamine. An amino acid residue indicated as Xaa at position 25 in the amino acid sequence as shown in SEQ ID NO: 1 is histidine or glutamine. An amino acid residue indicated as Xaa at position 28 in the amino acid sequence as shown in SEQ ID NO: 1 is glutamine, lycine, arginine, isoleucine, or threonine. An amino acid residue indicated as Xaa at position 30 in the amino acid sequence as shown in SEQ ID NO: 1 is leucine, valine, or isoleucine. An amino acid residue indicated as Xaa at position 31 in the amino acid sequence as shown in SEQ ID NO: 1 is leucine, valine, or isoleucine. An amino acid residue indicated as Xaa at position 32 in the amino acid sequence as shown in SEQ ID NO: 1 is glutamic acid or aspartic acid. An amino acid residue indicated as Xaa at position 34 in the amino acid sequence as shown in SEQ ID NO: 1 is serine, alanine, or threonine.

The "another amino acid residue" after substitution of the amino acid in the 30th position from the N terminus of the sequence shown in SEQ ID NO: 1 is different from the amino acid in the wild-type CDC123 protein. In the wild-type CDC123 proteins, the amino acid in the 30th position is not particularly limited, and it is often leucine, valine, or isoleucine. When the amino acid in the 30th position in a certain wild-type CDC123 protein is leucine, for example, the mutant CDC123 protein comprises an amino acid sequence in which leucine in the 30th position has been substituted with an amino acid residue other than leucine. In such a case, another amino acid residue other than leucine is not particularly limited, and it is preferably an amino acid other than valine and isoleucine. In the mutant CDC123 protein, the amino acid after substitution mutation is more preferably cysteine.

As a method of substitution of the amino acid in the 30th position from the N terminus of the sequence shown in SEQ ID NO: 1 with another amino acid residue, a conventional genetic engineering technique can be adequately employed. Specifically, a nucleotide sequence of a wild-type gene encoding a target protein into which a mutation is to be introduced is identified, and a mutation can be introduced to encode a protein after the substitution with the use of, for example, a site-directed mutagenesis kit. The gene into which the mutation has been introduced can be recovered in accordance with a conventional technique. For example, the gene can be integrated into an expression vector and recovered in that state. A mutation can be introduced into a gene by a conventional technique, such as the Kunkel method or the Gapped duplex method, or a method in accordance therewith. For example, a mutation can be introduced with the use of a mutagenesis kit that adopts a site-directed mutagenesis technique (e.g., Mutan-K and Mutan-G, Takara Bio Inc.) or an LA PCR in vitro Mutagenesis series kit (Takara Bio Inc.).

In the CDC123 protein derived from *Saccharomyces cerevisiae*, more specifically, the amino acid in the 30th position is leucine. SEQ ID NO: 2 and SEQ ID NO: 3 show the nucleotide sequence encoding the mutant CDC123 protein derived from *Saccharomyces cerevisiae* comprising a substitution of leucine in the 30th position with cysteine and the amino acid sequence of the mutant CDC123 protein, respectively. In the amino acid sequence of the mutant CDC123 protein as shown in SEQ ID NO: 3, the amino acid in the 30th position in SEQ ID NO: 1 corresponds to the amino acid in the 324th position from the N terminus. Specifically, cysteine in the 324th position in the amino acid sequence as shown in SEQ ID NO: 3 is leucine in the wild-type protein.

The mutant CDC123 protein is not limited to the protein comprising the amino acid sequence as shown in SEQ ID NO: 3. For example, it may be a protein comprising an amino acid sequence having 70% or higher identity to the amino acid sequence as shown in SEQ ID NO: 3, provided that cysteine in the 324th position is maintained. As described above, the degree of sequence identity may be 70% or higher, preferably 80% or higher, more preferably 85% or higher, further preferably 90% or higher, and most preferably 95% or higher. The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

The mutant CDC123 protein is not limited to the protein comprising the amino acid sequence as shown in SEQ ID NO: 3. As long as cysteine in the 324th position is maintained, a protein may comprise an amino acid sequence derived from the amino acid sequence as shown in SEQ ID NO: 3 by substitution, deletion, insertion, or addition of 1 or a plurality of amino acids and preferably 1 or several amino acids. The term "several" used herein refers to, for example, 2 to 40, preferably 2 to 30, more preferably 2 to 20, further preferably 2 to 10, and most preferably 2 to 5.

In addition, the mutant CDC123 protein is not limited to the protein encoded by the nucleotide sequence as shown in SEQ ID NO: 2. For example, it may be a protein encoded by a polynucleotide hybridizing under stringent conditions to the full-length sequence or a partial sequence of a complementary strand of DNA comprising the nucleotide sequence as shown in SEQ ID NO: 2, provided that the protein maintaining cysteine in the 324th position is encoded. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and temperature is 42° C. to 68° C. and preferably 42° C. to 65° C. Further specifically, hybridization is carried out in the presence of 5×SSC (83 mM NaCl, 83 mM sodium citrate) at 42° C.

In the case of the mutant CDC123 protein comprising an amino acid sequence other than the amino acid sequence as shown in SEQ ID NO: 3 or the mutant CDC123 protein encoded by a nucleotide sequence other than the nucleotide sequence as shown in SEQ ID NO: 2, as described above, the position of the cysteine residue after the mutation may not be the 324th position.

The mutant CDC123 protein is not limited to one derived from *Saccharomyces cerevisiae*. The origin thereof is not limited, provided that the CDC123 protein has the conserved region comprising the amino acid sequence as shown in SEQ ID NO: 1 in which the amino acid in the 30th position from the N terminus has been substituted with another amino acid residue. For example, wild-type CDC123 proteins derived from various organism species can be identified from the databases storing amino acid sequences and nucleotide sequences on the basis of the amino acid sequence of the CDC123 protein derived from *Saccharomyces cerevisiae* or the nucleotide sequence encoding such CDC123 protein. From among the wild-type CDC123 proteins identified in the manner described above, those having the conserved region comprising the amino acid sequence as shown in SEQ ID NO: 1 may be subjected to substitution of the amino acid in the 30th position, so that the mutant CDC123 protein and the mutant gene 1 encoding such mutant CDC123 protein can be obtained.

For example, the databases may be searched on the basis of the amino acid sequence of the CDC123 protein derived from *Saccharomyces cerevisiae*. Thus, wild-type CDC123 proteins each having the conserved region comprising the amino acid sequence of SEQ ID NO: 1 can be identified as shown in Table 1 (lines 2 to 13). Table 1 also shows the amino acid sequences comprising such conserved region.

TABLE 1

| Gene name | Sequence | SEQ ID NO: |
|---|---|---|
| Mutant CDC123 protein | EDYELRLVTRHNTGRFASKEHSENHVPQ DCVEASLNPEAIRELTQKWKELLSQQAK E-ESSDSESET | 10 |
| Cdc 123p [Saccharomyces cerevisiae YJM1381] | EDYELRLVTRHNTGRFASKEHSENHVPQ DLVEASLNPEAIRELTQKWKELLSQQAK E-ESSDSESET | 11 |
| CDC123-like protein [Saccharomyces kudriavzevii IFO 1802] | EDYELRLVTSHNTCRFASKEHSENHVPQ DLVEASLNPEAIRELTQKWKELLSQQTQ E-ESSDSEDGT | 12 |
| CDC123-like protein [Saccharomyces eubayanus] | EDYELRLVTRHNTGRFASKEHSENHVPQ DLVEAGLDPEAIRELTQKWRELLNQQTQ E-ESSGSEDEA | 13 |
| Cell division cycle protein 123 [Candida glabrata] | RDYELRLITENNIGRFASKEHSQNHVPK DVVDASLDPERIRELSQKWSELLLQQ E-----KESSDEE | 14 |
| Hypothetical protein KNAG_0B02750 [Kazachstania naganishii CBS 8797] | QDYELRLVKENNTARFASKEHSENHVPK DIVDASLDPNAIRDLAQKWKELLSQQQA EDSSSGSEEEA | 15 |
| Hypothetical protein NDAI_0A02840 [Naumovozyma dairenensis CBS 421] | KDYELRLVKENNVGRFVSKEHSENQVPK DLIDAALDPQAIKELTEKWKELLSRQEK D------EENK | 16 |
| Hypothetical protein TBLA_0F02200 [Tetrapisispora blattae CBS 6284] | RDYELRLVKRNNVARFASKEHSENQVPK DVVDASLDPNVIKELASKWKELLSQQEA D-TDSDSDSAE | 17 |
| Hypothetical protein NCAS_0E03830 [Naumovozyma castellii CBS 4309] | KDYELRLLTENNTGRFASKEHSENQVPR DLVDASLNPDAIRELTQKWKDLLSRQNG SGSDTESESES | 18 |
| Hypothetical protein TDEL_0C02280 [Torulaspora delbrueckii] | EDYELRIVPENNVARFATKEHSENHVPK DVLEASLNPEAIKELSEKWQELLRCQEL E-DDSDNE--- | 19 |
| Hypothetical protein KAFR_0L01360 [Kazachstania africana CBS 2517] | KDYELRLVLENNTARFASKEHSENQVPR DVVDATTDPNAIRELIGKWKELLEQQ E---EDTDSD--- | 20 |
| Hypothetical protein TPHA_0A03030 [Tetrapisispora phaffii | DDYELRLLTETNVGRFAHKEHSENQVPI DIVEASLNPDAIKELADKWSELLKKQDD Y--DSDSHDN- | 21 |

TABLE 1-continued

| Gene name | Sequence | SEQ ID NO: |
|---|---|---|
| CBS 4417] | | |
| Hypothetical protein KpoI_1019p20 [Vanderwaltozyma polyspora DSM 70294] | EDYEFRLIKENNVGRFACKEHSENQVPT DIVEASLNPEAIRELTQKWKELLSKQSM E-EDSSSDSNE | 22 |

Specifically, the mutant CDC123 protein may comprise an amino acid sequence comprising, for example, a substitution of an amino acid in SEQ ID NOs: 11 to 22 corresponding to the amino acid in the 30th position from the N terminus of the sequence in SEQ ID NO: 1 with another amino acid residue and preferably with cysteine.

<Mutant Gene 2>

The mutant gene 2 encodes a mutant SUI3 protein comprising a substitution of a particular amino acid with another amino acid in the β subunit of the translation initiator eIF2. The SUI3 protein is associated with the mechanism of eIF2 that detects an initiation codon as the β subunit of the translation initiator eIF2. The systematic name of the gene encoding the SUI3 protein is YPL237W.

The mutant SUI3 protein has a substitution mutation of a particular amino acid residue in the vicinity of the N terminus of a functional domain as a transcription initiator. A region comprising such mutation is conserved among many SUI3 proteins derived from different organism species. SEQ ID NO: 4 represents a conserved region comprising such mutation (a consensus sequence). The mutant SUI3 protein can be defined to comprise an amino acid sequence comprising a substitution of the amino acid in the 43rd position from the N terminus in SEQ ID NO: 4 with another amino acid residue.

The conserved region comprising the amino acid sequence as shown in SEQ ID NO: 4 is defined to be a region of 48 amino acid residues from the N terminus (the left end) in the amino acid sequences shown in the Table 2 below (lines 2 to 13). An amino acid residue indicated as Xaa at position 2 in the amino acid sequence as shown in SEQ ID NO: 4 is aspartic acid or glutamic acid. An amino acid residue indicated as Xaa at position 3 in the amino acid sequence as shown in SEQ ID NO: 4 is isoleucine, valine, leucine, or alanine. An amino acid residue indicated as Xaa at position 4 in the amino acid sequence as shown in SEQ ID NO: 4 is alanine, threonine, or serine. An amino acid residue indicated as Xaa at position 5 in the amino acid sequence as shown in SEQ ID NO: 4 is glutamic acid or aspartic acid. An amino acid residue indicated as Xaa at position 6 in the amino acid sequence as shown in SEQ ID NO: 4 is alanine or valine. An amino acid residue indicated as Xaa at position 7 in the amino acid sequence as shown in SEQ ID NO: 4 is leucine or phenylalanine. An amino acid residue indicated as Xaa at position 9 in the amino acid sequence as shown in SEQ ID NO: 4 is glutamic acid or leucine. An amino acid residue indicated as Xaa at position 11 in the amino acid sequence as shown in SEQ ID NO: 4 is serine, threonine, or lycine. An amino acid residue indicated as Xaa at position 19 in the amino acid sequence as shown in SEQ ID NO: 4 is threonine, serine, or alanine. An amino acid residue indicated as Xaa at position 20 in the amino acid sequence as shown in SEQ ID NO: 4 is lycine, alanine, or proline. An amino acid residue indicated as Xaa at position 21 in the amino acid sequence as shown in SEQ ID NO: 4 is aspartic acid, histidine, glutamic acid, or valine. An amino acid residue indicated as Xaa at position 22 in the amino acid sequence as shown in SEQ ID NO: 4 is serine, valine, threonine, or alanine. An amino acid residue indicated as Xaa at position 23 in the amino acid sequence as shown in SEQ ID NO: 4 is serine, alanine, threonine, aspartic acid, glutamic acid, or asparagine. An amino acid residue indicated as Xaa at position 24 in the amino acid sequence as shown in SEQ ID NO: 4 is valine or leucine. An amino acid residue indicated as Xaa at position 26 in the amino acid sequence as shown in SEQ ID NO: 4 is alanine, aspartic acid, or glutamic acid. An amino acid residue indicated as Xaa at position 29 in the amino acid sequence as shown in SEQ ID NO: 4 is lycine or glutamic acid. An amino acid residue indicated as Xaa 30 in the amino acid sequence as shown in SEQ ID NO: 4 is glutamine or glutamic acid. An amino acid residue indicated as Xaa at position 33 in the amino acid sequence as shown in SEQ ID NO: 4 is lycine, arginine, or serine. An amino acid residue indicated as Xaa at position 36 in the amino acid sequence as shown in SEQ ID NO: 4 is leucine or valine. An amino acid residue indicated as Xaa at position 37 in the amino acid sequence as shown in SEQ ID NO: 4 is aspartic acid, asparagine, or lycine. An amino acid residue indicated as Xaa at position 38 in the amino acid sequence as shown in SEQ ID NO: 4 is asparagine, serine, or valine. An amino acid residue indicated as Xaa at position 39 in the amino acid sequence as shown in SEQ ID NO: 4 is valine, isoleucine, aspartic acid, or alanine. An amino acid residue indicated as Xaa at position 40 in the amino acid sequence as shown in SEQ ID NO: 4 is aspartic acid, glutamic acid, threonine, serine, glycine, or valine. An amino acid residue indicated as Xaa at position 41 in the amino acid sequence as shown in SEQ ID NO: 4 is alanine, glycine, serine, glutamic acid, threonine, alanine, aspartic acid, or valine. An amino acid residue indicated as Xaa at position 42 in the amino acid sequence as shown in SEQ ID NO: 4 is glutamic acid, asparagine, or aspartic acid. An amino acid residue indicated as Xaa at position 43 in the amino acid sequence as shown in SEQ ID NO: 4 is serine or asparagine. An amino acid residue indicated as Xaa at position 44 in the amino acid sequence as shown in SEQ ID NO: 4 is lycine, serine, glutamic acid, or asparagine. An amino acid residue indicated as Xaa at position 45 in the amino acid sequence as shown in SEQ ID NO: 4 is glutamic acid, lycine, or aspartic acid. An amino acid residue indicated as Xaa at position 46 in the amino acid sequence as shown in SEQ ID NO: 4 is glycine, alanine, threonine, aspartic acid, serine, or glutamic acid. An amino acid residue indicated as Xaa at position 47 in the amino acid sequence as shown in SEQ ID NO: 4 is threonine or serine. An amino acid residue indicated as Xaa at position 48 in the amino acid sequence as shown in SEQ ID NO: 4 is proline or threonine.

The "another amino acid residue" after substitution of the amino acid in the 43rd position from the N terminus of the sequence shown in SEQ ID NO: 4 is different from the amino acid in the wild-type SUI3 protein. In the wild-type SUI3 proteins, the amino acid in the 43rd position is not particularly limited, and it is often serine or asparagine. When the amino acid in the 43rd position in a certain wild-type SUI3 protein is serine, for example, the mutant SUI3 protein comprises an amino acid sequence in which serine in the 43rd position has been substituted with an amino acid residue other than serine. In such a case, another amino acid residue other than serine is not particularly limited, and it is preferably an amino acid other than asparagine. In the mutant SUI3 protein, the amino acid after substitution mutation is more preferably threonine.

As a method of substitution of the amino acid in the 43rd position from the N terminus of the sequence shown in SEQ ID NO: 4 with another amino acid residue, a conventional genetic engineering technique can be adequately employed. Specifically, a nucleotide sequence of a wild-type gene encoding a target protein into which a mutation is to be introduced is identified, and a mutation can be introduced to encode a protein after the substitution with the use of, for example, a site-directed mutagenesis kit. The gene into which the mutation has been introduced can be recovered in accordance with a conventional technique. For example, the gene can be integrated into an expression vector and recovered in that state. A mutation can be introduced into a gene by a conventional technique, such as the Kunkel method or the Gapped duplex method, or a method in accordance therewith. For example, a mutation can be introduced with the use of a mutagenesis kit that adopts a site-directed mutagenesis technique (e.g., Mutan-K and Mutan-G, Takara Bio Inc.) or an LA PCR in vitro Mutagenesis series kit (Takara Bio Inc.).

In the SUI3 protein derived from *Saccharomyces cerevisiae*, more specifically, the amino acid in the 43rd position is serine. SEQ ID NO: 5 and SEQ ID NO: 6 show the nucleotide sequence encoding the mutant SUI3 protein derived from *Saccharomyces cerevisiae* comprising substitution of serine in the 43rd position with threonine and the amino acid sequence of the mutant SUI3 protein, respectively. In the amino acid sequence of the mutant SUI3 protein as shown in SEQ ID NO: 6, the amino acid in the 43rd position in SEQ ID NO: 4 corresponds to the amino acid in the 112th position from the N terminus. Specifically, threonine in the 112th position in the amino acid sequence as shown in SEQ ID NO: 6 is serine in the wild-type protein.

The mutant SUI3 protein is not limited to the protein comprising the amino acid sequence as shown in SEQ ID NO: 6. For example, it may be a protein comprising an amino acid sequence having 70% or higher identity to the amino acid sequence as shown in SEQ ID NO: 6, provided that threonine in the 112th position is maintained. As described above, the degree of sequence identity may be 70% or higher, preferably 80% or higher, more preferably 85% or higher, further preferably 90% or higher, and most preferably 95% or higher. The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

The mutant SUI3 protein is not limited to the protein comprising the amino acid sequence as shown in SEQ ID NO: 6. For example, it may be a protein comprising an amino acid sequence derived from the amino acid sequence as shown in SEQ ID NO: 6 by substitution, deletion, insertion, or addition of 1 or a plurality of and preferably 1 or several amino acids, provided that threonine in the 112th position is maintained. The term "several" used herein refers to, for example, 2 to 30, preferably 2 to 20, more preferably 2 to 10, and most preferably 2 to 5.

In addition, the mutant SUI3 protein is not limited to the protein encoded by the nucleotide sequence as shown in SEQ ID NO: 5. As long as a protein maintaining threonine in the 112th position is encoded, for example, it may be a protein encoded by a polynucleotide hybridizing under stringent conditions to the full-length sequence or a partial sequence of a complementary strand of DNA comprising the nucleotide sequence as shown in SEQ ID NO: 5. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and temperature is 42° C. to 68° C. and preferably 42° C. to 65° C. Further specifically, hybridization is carried out in the presence of 5×SSC (83 mM NaCl, 83 mM sodium citrate) at 42° C.

In the case of the mutant SUI3 protein comprising an amino acid sequence other than the amino acid sequence as shown in SEQ ID NO: 6 or the mutant SUI3 protein encoded by a nucleotide sequence other than the nucleotide sequence as shown in SEQ ID NO: 5, as described above, the position of the threonine residue after the mutation may not be the 112th position.

The mutant SUI3 protein is not limited to one derived from *Saccharomyces cerevisiae*. The origin thereof is not limited, provided that the SUI3 protein has the conserved region comprising the amino acid sequence as shown in SEQ ID NO: 4 in which the amino acid in the 43rd position from the N terminus has been substituted with another amino acid residue. For example, wild-type SUI3 proteins derived from various organism species can be identified from the databases storing amino acid sequences and nucleotide sequences on the basis of the amino acid sequence of the SUI3 protein derived from *Saccharomyces cerevisiae* or the nucleotide sequence encoding such SUI3 protein. From among the wild-type SUI3 proteins identified in the manner described above, those having the conserved region comprising the amino acid sequence as shown in SEQ ID NO: 4 may be subjected to substitution of the amino acid in the 43rd position, so that the mutant SUI3 protein and the mutant gene 2 encoding such mutant SUI3 protein can be obtained.

For example, the databases may be searched on the basis of the amino acid sequence of the SUI3 protein derived from *Saccharomyces cerevisiae*. Thus, wild-type SUI3 proteins each having the conserved region comprising the amino acid sequence of SEQ ID NO: 4 can be identified as shown in Table 2 (lines 2 to 13). Table 2 also shows the amino acid sequences comprising such conserved region.

TABLE 2

| Gene name | Sequence | SEQ ID NO: |
|---|---|---|
| Mutant SUI3 protein | KE-PTDDIAEALGELSLKKKKKK-TK DSSVDAFEKELAKAGLDNVD-AE--T KEGTP--S--ANS-SIQQEVGLPYSE LL | 23 |
| Sui3p [*Saccharomyces cerevisiae* YJM450] | KE-PTDDIAEAFGELSLKKKKKK-TK DSSVDAFEKELAKAGLDNVD-AE--S KEGTP--S--ANS-SIQQEVGLPYSE LL | 24 |

TABLE 2-continued

| Gene name | Sequence | SEQ ID NO: |
|---|---|---|
| SUI3-like protein [*Saccharomyces eubayanus*] | TE-PTDDIAEALGELSLKKKKKK-TK DSSVDAFEKELAKAGLDNVD-AE--S KEATP--A--ASA-SIQQEVGLPYPE LL | 25 |
| sui3p [*Saccharomyces arboricola* H-6] | KG-PTDDIAEALGELSLKKKKKK-TK DSSVDAFEKELAKAGLDSVE-GE--S KEATP--V--ASS-SIQQEVGLPYPE LL | 26 |
| Hypothetical protein KAFR_0F01140 [*Kazachstania africana* CBS 2517] | DN-TTDDITEALGELSLKKKKKK-TK DVALDDFEKELAKAG---VT-SE--S KETTP--Q--NIS-VVQQEAGLPYDK LL | 27 |
| Hypothetical protein KNAG_0D00820 [*Kazachstania naganishii* CBS 8797] | DG-ELDDVSEALGELTLKKKKKK-SK DSTLDDFEKELARAG---IN-EE--S SKDST--P--TGE-IGNDEVGLPYAD LL | 28 |
| Hypothetical protein NCAS_0G01200 [*Naumovozyma castellii* CBS 4309] | NN-SVDELSDVLGDLTIKKKKKK-AA HVDVDAFEKELAKAG---VS--TE-S KEATP--SGDNES-SIQNSIGLPYPE LL | 29 |
| Hypothetical protein TDEL_0A06770 [*Torulaspora delbrueckii*] | SD-SVDDISEALGELKLKKKKKK-AK DTDLDDFEQQLAKAGVNVDE-AN--N KEATP--T--VDS-ALQQEVGLAYPE LL | 30 |
| Hypothetical protein NDAI_0F01330 [*Naumovozyma dairenensis* CBS 421] | NNTSVDDLSDVLGDLTLKKKKKK-SK EATTDDFEKELAKAG---VS-T---S KDGTPISEGNSESETLQKEVGLPYPQ LL | 31 |
| Probable Eukaryotic translation initiation factor 2 subunit beta [*Zygosaccharomyces bailii* ISA1307] | SG-SVDEISEALGELKLKKKKK--SK ETEVDDFEQQLAKAGVKVAG-GN--S KESTP--V--AES-SIQQDVGLTYQD LL | 32 |
| Hypothetical protein TBLA_0A02260 [*Tetrapisispora blattae* CBS 6284] | NG-EIDEASEALGELSLKKKKKKkTK EANLDEFEKELAKAG---VVVDE--N KEETP--S--NES-TLQEDIGLPYQD LL | 33 |
| Hypothetical protein ZYGR_0AN00550 [*Zygosaccharomyces rouxii*] | SE-SVDEISEALGELKLKKKKK--SK EAEVDDFEKQLASAGVNVDG-GN--S QESTP--A--LES-SLQQDVGLSYPG LL | 34 |
| Hypothetical protein TPHA_0H01900 [*Tetrapisispora phaffii* CBS 4417] | D---VDDITEALGDLKLKKKKKK-AP VADVDEFEQELAKAG---VV-VDETS NEATP--G--HES-SLQQDVGLPYDK LL | 35 |

Specifically, the mutant SUI3 protein may comprise an amino acid sequence comprising, for example, a substitution of an amino acid in SEQ ID NOs: 24 to 35 corresponding to the amino acid in the 43rd position from the N terminus of SEQ ID NO: 4 with another amino acid residue and preferably with threonine.

<Mutant Gene 3>

The mutant gene 3 encodes a mutant FPK1 protein comprising a substitution of a particular amino acid with another amino acid in a serine/threonine protein kinase. The FPK1 protein phosphorylates a member of the aminophospholipid translocase family and regulates translocation and membrane asymmetry of a phospholipid. The FPK1 protein phosphorylates and inhibits an upstream inhibitory kinase Ypk1p. The systematic name of a gene encoding the FPK1 protein is YNR047W.

The mutant FPK1 protein comprises a substitution mutation of particular amino acid residues in the vicinity of the ATP-binding site and an active site within the catalytic domain of a serine/threonine protein kinase. A region comprising such mutation is conserved among many FPK1 proteins derived from different organism species. SEQ ID NO: 7 represents a conserved region within the catalytic domain comprising such mutation (a consensus sequence). The mutant FPK1 protein can be defined to comprise an amino acid sequence a substitution of the amino acid in the 31st position from the N terminus in SEQ ID NO: 7 with another amino acid residue.

The conserved region comprising the amino acid sequence as shown in SEQ ID NO: 7 is defined to be a region of 80 amino acid residues from the N terminus (the left end) in the amino acid sequences shown in the Table 3 below (lines 2 to 13). An amino acid residue indicated as Xaa at position 41 in the amino acid sequence as shown in SEQ ID NO: 7 is proline or isoleucine. An amino acid residue indicated as Xaa at position 46 in the amino acid sequence as shown in SEQ ID NO: 7 is glycine or alanine. An amino acid residue indicated as Xaa at position 47 in the amino acid sequence as shown in SEQ ID NO: 7 is aspartic acid, glutamic acid, or serine. An amino acid residue indicated as Xaa at position 48 in the amino acid sequence as shown in SEQ ID NO: 7 is asparagine, glutamic acid, or serine. An amino acid residue indicated as Xaa at position 49 in the amino acid sequence as shown in SEQ ID NO: 7 is threonine or serine. An amino acid residue indicated as Xaa at position 51 in the amino acid sequence as shown in SEQ ID NO: 7 is glutamic acid, glutamine, arginine, or leucine. An amino acid residue indicated as Xaa at position 54 in the amino acid sequence as shown in SEQ ID NO: 7 is threonine, serine, or cysteine. An amino acid residue indicated as Xaa at position 56 in the amino acid sequence as shown in SEQ ID NO: 7 is isoleucine or valine. An amino acid residue indicated as Xaa at position 59 in the amino acid sequence as shown in SEQ ID NO: 7 is asparagine, lycine, or serine. An amino acid residue indicated as Xaa at position 60 in the amino acid sequence as shown in SEQ ID NO: 7 is glutamic acid or aspartic acid. An amino acid residue indicated as Xaa 6 at position 2 in the amino acid sequence as shown in SEQ ID NO: 7 is serine, threonine, isoleucine, or asparagine. An amino acid residue indicated as Xaa at position 68 in the amino acid sequence as shown in SEQ ID NO: 7 is glutamic acid or aspartic acid. An amino acid residue indicated as Xaa at position 69 in the amino acid sequence as shown in SEQ ID NO: 7 is isoleucine or valine. An amino acid residue indicated as Xaa at position 70 in the amino acid sequence as shown in SEQ ID NO: 7 is serine or glycine. An amino acid residue indicated as Xaa at position 72 in the amino acid sequence as shown in SEQ ID NO: 7 is threonine, asparagine, alanine, or serine. An amino acid residue indicated as Xaa at position 78 in the amino acid sequence as shown in SEQ ID NO: 7 is lycine or arginine. An amino acid residue indicated as Xaa at position 79 in the amino acid sequence as shown in SEQ ID NO: 7 is lycine or arginine.

The "another amino acid residue" after substitution of the amino acid in the 31st position from the N terminus of SEQ ID NO: 7 is different from the amino acid in the wild-type FPK1 protein. In the wild-type FPK1 proteins, the amino acid in the 31st position is not particularly limited, and it is often glycine. When the amino acid in the 31st position in a certain wild-type FPK1 protein is glycine, for example, the mutant FPK1 protein comprises an amino acid sequence in which glycine in the 31st position has been substituted with an amino acid residue other than glycine. In such a case, another amino acid residue other than glycine is not particularly limited, and it is preferably glutamic acid.

As a method of substitution of the amino acid in the 31st position from the N terminus of the sequence shown in SEQ ID NO: 7 with another amino acid residue, a conventional genetic engineering technique can be adequately employed. Specifically, a nucleotide sequence of a wild-type gene encoding a target protein into which a mutation is to be introduced is identified, and a mutation can be introduced to encode a protein after the substitution with the use of, for example, a site-directed mutagenesis kit. The gene into which the mutation has been introduced can be recovered in accordance with a conventional technique. For example, the gene can be integrated into an expression vector and recovered in that state. A mutation can be introduced into a gene by a conventional technique, such as the Kunkel method or the Gapped duplex method, or a method in accordance therewith. For example, a mutation can be introduced with the use of a mutagenesis kit that adopts a site-directed mutagenesis technique (e.g., Mutan-K and Mutan-G, Takara Bio Inc.) or an LA PCR in vitro Mutagenesis series kit (Takara Bio Inc.).

In the FPK1 protein derived from *Saccharomyces cerevisiae*, more specifically, the amino acid in the 31st position is glycine. SEQ ID NO: 8 and SEQ ID NO: 9 show the nucleotide sequence encoding the mutant FPK1 protein derived from *Saccharomyces cerevisiae* comprising a substitution of glycine in the 31st position with glutamic acid and the amino acid sequence of the mutant FPK1 protein, respectively. In the amino acid sequence of the mutant FPK1 protein as shown in SEQ ID NO: 9, the amino acid in the 31st position in SEQ ID NO: 7 corresponds to the amino acid in the 704th position from the N terminus. Specifically, glutamic acid in the 704th position in the amino acid sequence as shown in SEQ ID NO: 9 is glycine in the wild-type protein.

The mutant FPK1 protein is not limited to the protein comprising the amino acid sequence as shown in SEQ ID NO: 9. For example, it may be a protein comprising an amino acid sequence having 70% or higher identity to the amino acid sequence as shown in SEQ ID NO: 9, provided that glutamic acid in the 704th position is maintained. As described above, the degree of sequence identity may be 70% or higher, preferably 80% or higher, more preferably 85% or higher, further preferably 90% or higher, and most preferably 95% or higher. The degree of sequence identity can be determined using the BLASTN or BLASTX Program equipped with the BLAST algorithm (at default settings). The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

The mutant FPK1 protein is not limited to the protein comprising the amino acid sequence as shown in SEQ ID NO: 9. For example, it may be a protein comprising an amino acid sequence derived from the amino acid sequence as shown in SEQ ID NO: 9 by substitution, deletion, insertion, or addition of 1 or a plurality of and preferably 1 or several amino acids, provided that glutamic acid in the 704th position is maintained. The term "several" used herein refers to, for example, 2 to 90, preferably 2 to 80, more preferably 2 to 70, more preferably 2 to 60, more preferably 2 to 50, more preferably 2 to 40, more preferably 2 to 30, more preferably 2 to 20, more preferably 2 to 10, and most preferably 2 to 5.

Furthermore, the mutant FPK1 protein is not limited to the protein encoded by the nucleotide sequence as shown in SEQ ID NO: 8. For example, it may be a protein encoded by a polynucleotide hybridizing under stringent conditions to the full-length sequence or a partial sequence of a complementary strand of DNA comprising the nucleotide sequence as shown in SEQ ID NO: 8, provided that the protein maintaining the glutamic acid in the 704th position is encoded. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and temperature is 42° C. to 68° C. and preferably 42° C. to 65° C. Further specifically, hybridization is carried out in the presence of 5×SSC (83 mM NaCl, 83 mM sodium citrate) at 42° C.

In the case of the mutant SUI3 protein comprising an amino acid sequence other than the amino acid sequence as shown in SEQ ID NO: 9 or the mutant SUI3 protein encoded by a nucleotide sequence other than the nucleotide sequence as shown in SEQ ID NO: 8, as described above, the position of the threonine residue after the mutation may not be the 704th position.

The mutant FPK1 protein is not limited to one derived from *Saccharomyces cerevisiae*. The origin thereof is not limited, provided that the FPK1 protein has the conserved region comprising the amino acid sequence as shown in SEQ ID NO: 7 in which the amino acid in the 31st position from the N terminus has been substituted with another amino acid residue. For example, wild-type FPK1 proteins derived from various organism species can be identified from the databases storing amino acid sequences and nucleotide sequences on the basis of the amino acid sequence of the FPK1 protein derived from *Saccharomyces cerevisiae* or the nucleotide sequence encoding such FPK1 protein. From among the wild-type FPK1 proteins identified in the manner described above, those having the conserved region comprising the amino acid sequence as shown in SEQ ID NO: 7 may be subjected to substitution of the amino acid in the 31st position, so that the mutant FPK1 protein and the mutant gene 3 encoding such mutant FPK1 protein can be obtained.

For example, the databases may be searched on the basis of the amino acid sequence of the FPK1 protein derived from *Saccharomyces cerevisiae*. Thus, wild-type FPK1 proteins each having the conserved region comprising the amino acid sequence of SEQ ID NO: 7 can be identified as shown in Table 3 (lines 2 to 13). Table 3 also shows the amino acid sequences comprising such conserved region.

TABLE 3

| Gene name | Sequence | SEQ ID NO: |
|---|---|---|
| Mutant FPK1 protein | TNSFVGTEEYIAPEVIRGNGHTAAVD WWTLEILIYEMLFGFTPFKGDNTNET FTNILKNEVSFPNNNEISRTCKDLIK KL | 36 |
| Fpk1p [*Saccharomyces cerevisiae* YJM1078] | TNSFVGTEEYIAPEVIRGNGHTAAVD WWTLGILIYEMLFGFTPFKGDNTNET FTNILKNEVSFPNNNEISRTCKDLIK KL | 37 |
| Flippase kinase 1 [*Candida glabrata*] | TNSFVGTEEYIAPEVIRGNGHTAAVD WWTLGILIYEMLFGFTPFKGENTNET FSNILKKDVTFPNNNEVSRNCKDLIK KL | 38 |
| Hypothetical protein TDEL_0A07860 [*Torulaspora delbrueckii*] | TNSFVGTEEYIAPEVIRGNGHTAAVD WWTLGILTYEMLFGFTPFKGDNTNET FCNILKSEVTFPNNNEISRACKDLIK KL | 39 |
| Hypothetical protein NCAS_0A05570 [*Naumovozyma castellii* CBS 4309] | TNSFVGTEEYIAPEVIRGNGHTAAVD WWTLGILIYEMLFGFTPFKGSSSNET FSNILKNDVSFPNNNDISRNCKDLIK KL | 40 |
| LAFE_0C00628g1_1 [*Lachancea fermentati*] | TNSFVGTEEYIAPEVIRGNGHTAAVD WWTLGILIYEMLFGFTPFKGDNTNQT FSNILKNDVIFPNNNEISRTCKDLIK RL | 41 |
| LALA0S02e06326g1_1 [*Lachancea lanzarotensis*] | TNSFVGTEEYLAPEVIRGNGHTAAVD WWTLGILIYEMLFGFTPFKGDNTNRT FSNVLKNDVTFPNNNEISRSCKDLIR RL | 42 |
| LAQU0S09e04104g1_1 [*Lachancea quebecensis*] | TNSFVGTEEYIAPEVIRGNGHTAAVD WWTLGILIYEMLFGFTPFKADTTNKT FSNVLKNEVTFPNNNEISRNCKDLIK KL | 43 |
| LADA_0F15170g1_1 [*Lachancea dasiensis* CBS 10888] | TNSFVGTEEYIAPEVIRGNGHTAAVD WWTLGILIYEMLFGFTPFKGDNTNKT FSNVLKNDVNFPNNNEVSRSCKDLIR KL | 44 |
| KLTH0A07458p [*Lachancea thermotolerans* CBS 6340] | TNSFVGTEEYIAPEVIRGNGHTAAVD WWTLGILIYEMLFGFTPFKADTTNKT FSNVLKNEVTFPNNNEVSRNCKDLIK KL | 45 |
| LANO_0A00738g1_1 [*Lachancea nothofagi* CBS 11611] | TNSFVGTEEYIAPEVIRGNGHTAAVD WWTLGILIYEMLFGFTPFKGDNTNKT FSNVLKNEVSFPNNNEVSRSCKDLIR KL | 46 |
| Hypothetical protein Kpol_1028p16 [*Vanderwaltozyma polyspora* DSM 70294] | TNSFVGTEEYIAPEVIRGNGHTAAVD WWTLGILIYEMLFGFTPFKGDNTNET FCNVLKNDVNFPNNNEISRTCKDLIK KL | 47 |
| Hypothetical protein ZYGR_0AK07530 [*Zygosaccharomyces rouxii*] | TNSFVGTEEYIAPEVIRGNGHTAAVD WWTLGILIYEMLFGITPFKASNTNET FCNILKNEVTFPNNNDIGRSCKDLIK KL | 48 |

Specifically, the mutant FPK1 protein may comprise an amino acid sequence comprising a, for example, a substitution of an amino acid in SEQ ID NOs: 37 to 48 corresponding to the amino acid in the 31st position from the N terminus of the sequence shown in SEQ ID NO: 7 with another amino acid residue and preferably with threonine.

<Mutant Yeast Strain>

The mutant yeast strain according to the present invention comprises the mutant gene described above and has xylose-metabolizing ability. The mutant yeast strain comprising the mutant gene described above can be produced by, for example, a method of introducing the mutation as described above so as to modify the wild-type gene endogenous in the genome. Specifically, the mutant yeast strain comprising the mutant gene according to the present invention can be produced by the technique of site-directed mutagenesis as described above.

A mutant yeast strain of interest can also be produced via homologous recombination between the mutant gene prepared in advance and the wild-type gene in the genome. Alternatively, the mutant yeast strain comprising the mutant gene according to the present invention may be produced by deleting the wild-type gene from the genome and introducing the mutant gene thereinto in an expressible manner. Alternatively, the mutant yeast strain comprising the mutant gene according to the present invention may be produced by introducing the mutant gene so as to overexpress the same in the genome while refraining from deleting the wild-type gene from the genome. Also, a mutant yeast strain comprising the mutant gene described above can be produced by mutagen treatment.

Mutagen treatment may be carried out with the use of chemical mutagenic agents typified by EMS (ethylmethane sulfonate), 5-bromouracil, 2-aminopurine, hydroxylamine, N-methyl-N'-nitro-N-nitrosoguanidine, and other carcinogenic compounds, via treatment with radiation typified by X rays, alpha rays, beta rays, gamma rays, and ion beams, or via ultraviolet treatment.

The term "yeast strain having xylose-metabolizing ability" used herein refers to: a yeast strain that has acquired the xylose-assimilating ability as a result of introduction of a xylose metabolism-associated enzyme gene into a yeast strain that does not inherently has xylose-metabolizing ability (synonymous with "assimilating ability"); and a yeast strain that inherently comprises a xylose metabolism-associated enzyme gene and has the xylose-metabolizing ability.

Examples of yeast strains having xylose-metabolizing ability include: a yeast strain that has been provided with xylose-assimilating ability as a result of introduction of a xylose isomerase gene into a yeast strain that does not inherently has xylose-metabolizing ability; and a yeast strain that has been provided with xylose-metabolizing ability as a result of introduction of another xylose metabolism-associated gene.

The mutant yeast strain according to the present invention may have an ability of metabolizing xylose (i.e., the xylose-metabolizing ability), specifically, it can assimilate xylose contained in a medium to generate ethanol. Xylose contained in a medium may be obtained by saccharification of xylan or hemicellulose comprising xylose as a constituent sugar. Alternatively, it may be supplied to a medium as a result of saccharification of xylan or hemicellulose contained in a medium by a saccharifying enzyme. The latter case refers to the so-called simultaneous saccharification and fermentation process.

The xylose isomerase gene (the XI gene) is not particularly limited, and a gene originating from any organism species may be used. For example, a plurality of the xylose isomerase genes derived from the intestinal protozoa of *Reticulitermes speratus* disclosed in JP 2011-147445 A can be used without particular limitation. Examples of the xylose isomerase genes that can be used include a gene derived from the anaerobic fungus *Piromyces* sp. strain E2 (JP 2005-514951 A), a gene derived from the anaerobic fungus *Cyllamyces aberensis*, a gene derived from a bacterial strain (i.e., *Bacteroides thetaiotaomicron*), a gene derived from a bacterial strain (i.e., *Clostridium phytofermentans*), and a gene derived from the *Streptomyces murinus* cluster.

Specifically, a xylose isomerase gene derived from the intestinal protozoa of *Reticulitermes speratus* may preferably be used. SEQ ID NO: 49 and SEQ ID NO: 50 show the nucleotide sequence of the coding region of the xylose isomerase gene derived from the intestinal protozoa of *Reticulitermes speratus* and the amino acid sequence of a protein encoded by such gene, respectively.

The xylose isomerase gene is not limited to the gene identified by SEQ ID NO: 49 and SEQ ID NO: 50. It may be a paralogous gene or a homologous gene in the narrow sense having different nucleotide and amino acid sequences.

The xylose isomerase gene is not limited to the gene identified by SEQ ID NO: 49 and SEQ ID NO: 50. For example, it may be a gene comprising an amino acid sequence having 70% or higher, preferably 80% or higher, more preferably 90% or higher, and most preferably 95% or higher sequence similarity or identity to the amino acid sequence as shown in SEQ ID NO: 50 and encoding a protein having xylose isomerase activity. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the xylose isomerase gene is not limited to the gene identified by SEQ ID NO: 49 and SEQ ID NO: 50. For example, it may be a gene comprising an amino acid sequence derived from the amino acid sequence as shown in SEQ ID NO: 50 by substitution, deletion, insertion, or addition of one or several amino acids and encoding the protein having xylose isomerase activity. The term "several" used herein refers to, for example, 2 to 30, preferably 2 to 20, more preferably 2 to 10, and most preferably 2 to 5.

Furthermore, the xylose isomerase gene is not limited to the gene identified by SEQ ID NO: 49 and SEQ ID NO: 50. For example, it may be a gene hybridizing under stringent conditions to the full-length sequence or a partial sequence of a complementary strand of DNA comprising the nucleotide sequence as shown in SEQ ID NO: 49 and encoding the protein having xylose isomerase activity. Under "stringent conditions," so-called specific hybrids are formed, but non-specific hybrids are not formed. For example, such conditions can be adequately determined with reference to Molecular Cloning: A Laboratory Manual (Third Edition).

Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM and preferably 25 to 300 mM, and the temperature is 42° C. to 68° C. and preferably 42° C. to 65° C. Further specifically, hybridization is carried out in the presence of 5×SSC (83 mM NaCl, 83 mM sodium citrate) at 42° C.

As described above, whether or not a gene comprising a nucleotide sequence that differs from the sequence as shown in SEQ ID NO: 49 or a gene encoding an amino acid sequence that differs from the sequence as shown in SEQ ID NO: 50 would function as a xylose isomerase gene may be determined by, for example, preparing an expression vector comprising the gene of interest integrated into an adequate site between a promoter and a terminator, transforming an E. coli host using such expression vector, and assaying the xylose isomerase activity of the protein expressed. The term "xylose isomerase activity" refers to activity of isomerizing xylose into xylulose. Accordingly, xylose isomerase activity can be evaluated by preparing a xylose-containing solution as a substrate, allowing the target protein to react at an adequate temperature, and measuring the amount of xylose that has decreased and/or the amount of xylulose that has been generated.

In particular, a xylose isomerase gene preferably comprises an amino acid sequence derived from the amino acid sequence as shown in SEQ ID NO: 50 by introduction of a particular mutation into a particular amino acid residue and encodes a mutant xylose isomerase with improved xylose isomerase activity. A specific example of a gene encoding a mutant xylose isomerase is a gene encoding an amino acid sequence derived from the amino acid sequence as shown in SEQ ID NO: 50 by substitution of asparagine with cysteine in the 337th position. Xylose isomerase activity of such mutant xylose isomerase is superior to that of wild-type xylose isomerase. In addition, mutant xylose isomerase is not limited to the xylose isomerase resulting from substitution of asparagine with cysteine in the 337th position. It may be xylose isomerase resulting from substitution of asparagine with an amino acid residue other than cysteine in the 337th position, xylose isomerase resulting from substitution of an amino acid residue at a position different from the 337th position, in addition to substitution of asparagine in the 337th position, or xylose isomerase resulting from substitution of an amino acid residue other than cysteine in the 337th position.

Meanwhile, examples of xylose metabolism-associated genes other than the xylose isomerase gene include a xylose reductase gene encoding a xylose reductase that converts xylose into xylitol, a xylitol dehydrogenase gene encoding a xylitol dehydrogenase that converts xylitol into xylulose, and a xylulokinase gene encoding a xylulokinase that phosphorylates xylulose to produce xylulose 5-phosphate. Xylulose 5-phosphate produced by a xylulokinase enters the pentose phosphate pathway, and it is then metabolized therein.

Examples of xylose metabolism-associated genes include, but are not particularly limited to, a xylose reductase gene and a xylitol dehydrogenase gene derived from *Pichia stipitis* and a xylulokinase gene derived from *Saccharomyces cerevisiae* (see Eliasson A. et al., Appl. Environ. Microbiol., 66: 3381-3386; and Toivari M. N. et al., Metab. Eng., 3: 236-249). In addition, xylose reductase genes derived from *Candida tropicalis* and *Candida prapsilosis*, xylitol dehydrogenase genes derived from *Candida tropicalis* and *Candida prapsilosis*, and a xylulokinase gene derived from *Pichia stipitis* can be used.

Examples of yeast strains that inherently have xylose-metabolizing ability include, but are not particularly limited to, *Pichia stipitis, Candida tropicalis*, and *Candida prapsilosis*.

The mutant yeast strain according to the present invention may further comprise other gene(s) introduced thereinto, and such other gene(s) are not particularly limited. For example, a gene involved in the sugar metabolism of glucose may be introduced into such mutant yeast strain. For example, a mutant yeast strain can have β-glucosidase activity resulting from the introduction of the β-glucosidase gene.

The term "β-glucosidase activity" used herein refers to the activity of catalyzing a hydrolysis reaction of a β-glycoside bond of a sugar. Specifically, β-glucosidase is capable of degrading a cellooligosaccharide, such as cellobiose, into glucose. The β-glucosidase gene can be introduced in the form of a cell-surface display gene. The term "cell-surface display gene" used herein refers to a gene that is modified to display a protein to be encoded by the gene on a cell surface. For example, a cell-surface display β-glucosidase gene results from fusion of a β-glucosidase gene with a cell-surface localized protein gene. A cell-surface localized protein is fixed and present on a yeast cell surface layer. Examples include agglutinative proteins, such as α- or a-agglutinin and FLO proteins. In general, a cell-surface localized protein comprises an N-terminal secretory signal sequence and a C-terminal GPI anchor attachment signal sequence. While a cell-surface localized protein shares properties with a secretory protein in terms of the presence of a secretory signal, its secretory signal differs in that the cell-surface localized protein is transported while fixed to a cell membrane through a GPI anchor. When a cell-surface localized protein passes through a cell membrane, a GPI anchor attachment signal sequence is selectively cut, it binds to a GPI anchor at a newly protruded C-terminal region, and it is then fixed to the cell membrane. Thereafter, the root of the GPI anchor is cut by phosphatidylinositol-dependent phospholipase C (PI-PLC). Subsequently, a protein separated from the cell membrane is integrated into a cell wall, fixed onto a cell surface layer, and then localized on a cell surface layer (see, for example, JP 2006-174767 A).

The β-glucosidase gene is not particularly limited, and an example is a β-glucosidase gene derived from *Aspergillus aculeatus* (Murai et al., Appl. Environ. Microbiol., 64: 4857-4861). In addition, a β-glucosidase gene derived from *Aspergillus oryzae*, a β-glucosidase gene derived from *Clostridium cellulovorans*, and a β-glucosidase gene derived from *Saccharomycopsis fibligera* may be used.

In addition to or other than the β-glucosidase gene, a gene encoding another cellulase-constituting enzyme may have been introduced into the mutant yeast strain according to the present invention. Examples of cellulase-constituting enzymes other than 3-glucosidase include exo-cellobiohydrolases that liberate cellobiose from the terminus of crystalline cellulose (CBH1 and CBH2) and endo-glucanase (EG) that cannot degrade crystalline cellulose but cleaves a non-crystalline cellulose (amorphous cellulose) chain at random.

A particular example of another gene to be introduced into a mutant yeast strain is a gene capable of promoting the use of xylose in a medium. A further specific example thereof is a gene encoding xylulokinase having activity of generating xylulose-5-phosphate using xylulose as a substrate. The metabolic flux of the pentose phosphate pathway can be improved through the introduction of the xylulokinase gene.

Further, a gene encoding an enzyme selected from the group of enzymes constituting a non-oxidative process in the pentose phosphate pathway can be introduced into the mutant yeast strain according to the present invention. Examples of enzymes constituting a non-oxidative process in the pentose phosphate pathway include ribose-5-phosphate isomerase, ribulose-5-phosphate-3-epimerase, transketolase, and transaldolase. It is preferable that one or more genes encoding such enzymes be introduced, more preferable that two or more such genes be introduced in combination, further preferable that three or more genes be introduced in combination, and the most preferable that all of the genes above be introduced.

More specifically, the xylulokinase (XK) gene of any origin can be used without particular limitation. A wide variety of microorganisms, such as bacterial and yeast strains, which assimilate xylulose, possess the XK gene. Information concerning XK genes can be obtained by searching the website of NCBI or other institutions, according to need. Preferable examples of such genes include the XK genes derived from yeast strains, lactic acid bacteria, *E. coli* bacteria, and plants. An example of an XK gene is XKS1, which is an XK gene derived from the *S. cerevisiae* S288C strain (GenBank: Z72979) (the nucleotide sequence and the amino acid sequence in the CDS coding region).

More specifically, a transaldolase (TAL) gene, a transketolase (TKL) gene, a ribulose-5-phosphate epimerase (RPE) gene, and a ribose-5-phosphate ketoisomerase (RKI) gene of any origin can be used without particular limitation. A wide variety of organisms comprising the pentose phosphate pathway possess such genes. For example, a common yeast strain such as *S. cerevisiae* possesses such genes. Information concerning such genes can be obtained from the website of NCBI or other institutions, according to need. Genes belonging to the same genus as the host eukaryotic cells, such as eukaryotic or yeast cells, are preferable, and genes originating from the same species as the host eukaryotic cells are more preferable. A TAL1 gene, a TKL1 gene and a TKL2 gene, an RPE1 gene, and an RKI1 gene can be preferably used as the TAL gene, the TKL genes, the RPE gene, and the RKI gene, respectively. Examples of such genes include a TAL1 gene derived from the *S. cerevisiae* S288 strain (GenBank: U19102), a TKL1 gene derived from the *S. cerevisiae* S288 strain (GenBank: X73224), an RPE1 gene derived from the *S. cerevisiae* S288 strain (GenBank: X83571), and an RKI1 gene derived from the *S. cerevisiae* S288 strain (GenBank: Z75003).

When the mutant genes or the xylose metabolism-associated gene are to be introduced into a yeast strain, such genes may be simultaneously introduced thereinto, or such genes may be successively introduced with the use of different expression vectors.

Examples of host yeast strains that can be used include, but are not particularly limited to, *Candida Shehatae, Pichia stipitis, Pachysolen tannophilus, Saccharomyces cerevisiae*, and *Schizosaccharomyces pombe*, with *Saccharomyces cerevisiae* being particularly preferable. Experimental yeast strains may also be used from the viewpoint of experimental convenience, or industrial (practical) strains may also be used from the viewpoint of practical usefulness. Examples of industrial strains include yeast strains used for the production of wine, sake, and shochu.

Use of a host yeast strain having homothallic properties is preferable. According to the technique disclosed in JP 2009-34036 A, multiple copies of genes can be easily introduced into a genome with the use of a yeast strain having homothallic properties. The term "yeast strain having homothallic properties" has the same meaning as the term "homothallic yeast strain." Yeast strains having homothallic properties are not particularly limited, and any yeast strains can be used. An example of a yeast strain having homothallic properties is, but is not limited to, the *Saccharomyces cerevisiae* OC-2 train (NBRC2260). Examples of other yeast strains having homothallic properties include an alcohol-producing yeast (Taiken No. 396, NBRC0216) (reference: "*Alcohol kobo no shotokusei*" ("Various properties of alcohol-producing yeast"), Shuken Kaiho, No. 37, pp. 18-22, 1998.8), an ethanol-producing yeast isolated in Brazil and in Japan (reference: "*Brazil to Okinawa de bunri shita Saccharomyces cerevisiae yaseikabu no idengakuteki seishitsu*" ("Genetic properties of wild-type *Saccharomyces cerevisiae* isolated in Brazil and in Okinawa"), the Journal of the Japan Society for Bioscience, Biotechnology, and Agrochemistry, Vol. 65, No. 4, pp. 759-762, 1991.4), and 180 (reference: "*Alcohol Hakkoryoku no tsuyoi kobo no screening*" ("Screening of yeast having potent alcohol-fermenting ability"), the Journal of the Brewing Society of Japan, Vol. 82, No. 6, pp. 439-443, 1987.6). In addition, the HO gene may be introduced into a yeast strain exhibiting heterothallic phenotypes in an expressible manner, and the resulting strain can be used as a yeast strain having homothallic properties. That is, the term "yeast strain having homothallic properties" used herein also refers to a yeast strain into which the HO gene has been introduced in an expressible manner.

Promoters of genes to be introduced are not particularly limited. For example, promoters of the glyceraldehyde-3-phosphate dehydrogenase gene (TDH3), the 3-phosphoglycerate kinase gene (PGK1), and the high-osmotic pressure response 7 gene (HOR7) can be used. The promoter of the pyruvate decarboxylase gene (PDC1) is particularly preferable in terms of its high capacity for expressing target genes in a downstream region at high levels.

Specifically, such mutant gene may be introduced into the yeast genome together with an expression-regulated promoter or another expression-regulated region. Such mutant gene may be introduced into a host yeast genome in such a manner that expression thereof is regulated by a promoter or another expression-regulated region of a gene that is inherently present therein.

The mutant genes can be introduced into the genome by any conventional technique known as a yeast transformation technique. Specific examples include, but are not limited to, electroporation (Meth. Enzym., 194, p. 182, 1990), the spheroplast technique (Proc. Natl. Acad. Sci., U.S.A., 75, p. 1929, 1978), and the lithium acetate method (J. Bacteriology, 153, p. 163, 1983; Proc. Natl. Acad. Sci., U.S.A., 75, p. 1929, 1978; Methods in yeast genetics, 2000 Edition: A Cold Spring Harbor Laboratory Course Manual).

<Production of Ethanol>

When producing ethanol with the use of the mutant yeast strain described above, ethanol fermentation is carried out by culture in a medium containing at least xylose. Specifically, a medium in which ethanol fermentation is carried out contains, as a carbon source, at least metabolizable xylose. The medium may be supplemented with another carbon source, such as glucose, in advance.

A xylose, that is contained in a medium to be used for ethanol fermentation can be derived from a biomass. In other words, a medium to be used for ethanol fermentation may comprise a cellulosic biomass and hemicellulase that generates xylose, through saccharification of hemicellulose contained in a cellulosic biomass. The cellulosic biomass may have been subjected to a conventional pretreatment technique. Examples of pretreatment techniques include, but are not particularly limited to, degradation of a lignin with a microorganism and grinding of a cellulosic biomass. For example, a ground cellulosic biomass may be subjected to pretreatment, such as soaking thereof in a dilute sulfuric acid solution, alkaline solution, or ionic solution, hydrothermal treatment, or fine grinding. Thus, the efficiency of biomass saccharification can be improved.

When producing ethanol with the use of the mutant yeast strain described above, the medium may further comprise cellulose and cellulase. In such a case, the medium contains glucose generated by the action of cellulase imposed upon cellulose. When a medium used for ethanol fermentation contains cellulose, such cellulose can be derived from a biomass. In other words, a medium used for ethanol fermentation may comprise cellulase that is capable of saccharifying cellulase contained in a cellulosic biomass.

A saccharified solution resulting from saccharification of a cellulosic biomass may be added to the medium used for ethanol fermentation. In such a case, the saccharified solution contains remaining cellulose or cellulase and xylose derived from hemicellulose contained in a cellulosic biomass.

As described above, the method for producing ethanol according to the present invention comprises a step of ethanol fermentation involving the use of at least xylose, as a saccharide source. According to the method for producing ethanol with the use of the mutant yeast strain according to the present invention, ethanol fermentation is followed by recovery of ethanol from the medium. Ethanol may be recovered by any conventional means without particular limitation. After the completion of the process of ethanol fermentation mentioned above, for example, a liquid layer containing ethanol is separated from a solid layer containing the recombinant yeast strain or solid matter via solid-solution separation. Thereafter, ethanol contained in a liquid layer is separated and purified by distillation, so that highly purified ethanol can be recovered. The degree of ethanol purification can be adequately determined in accordance with the purpose of use of the ethanol.

The method for producing ethanol according to the present invention may employ the so-called simultaneous saccharification and fermentation process in which the step of saccharification of cellulose contained in a medium with a cellulase proceeds simultaneously with the step of ethanol fermentation involving the use of saccharide sources; i.e., xylose and glucose generated by saccharification. With the simultaneous saccharification and fermentation process, the step of saccharification of a cellulosic biomass is carried out simultaneously with the process of ethanol fermentation.

Methods of saccharification are not particularly limited. For example, an enzymatic method involving the use of a cellulase preparation, such as cellulase or hemicellulase, may be employed. A cellulase preparation contains a plurality of enzymes involved in degradation of a cellulose chain and a hemicellulose chain, and it exhibits a plurality of types of activity, such as endoglucanase activity, endoxylanase activity, cellobiohydrolase activity, glucosidase activity, and xylosidase activity. Cellulase preparations are not particularly limited, and examples include cellulases produced by *Trichoderma reesei* and *Acremonium cellulolyticus*. Commercially available cellulase preparations may also be used.

In the simultaneous saccharification and fermentation process, a cellulase preparation and the recombinant microorganism are added to a medium containing a cellulosic biomass (a biomass after pretreatment may be used), and the recombinant yeast strain is cultured at a given temperature. Culture may be carried out at any temperature without particular limitation, and the temperature may be 25° C. to 45° C. and preferably 30° C. to 40° C., from the viewpoint of ethanol fermentation efficiency. The pH level of the culture solution is preferably 4 to 6. Agitation or shake culture may be employed. Alternatively, the simultaneous saccharification and fermentation process may be carried out irregularly in such a manner that saccharification is first carried out at an optimal temperature for an enzyme (40° C. to 70° C.), temperature is lowered to a given level (30° C. to 40° C.), and a yeast strain is then added thereto.

The method for producing ethanol according to the present invention involves the use of the mutant yeast strain comprising the mutant gene described above. In comparison with the use of a xylose-metabolizing enzyme that does not comprise a mutant gene, accordingly, ethanol of higher concentration can be produced. More specifically, the mutant yeast strain comprising the mutant gene described above has an ability of producing ethanol from xylose via fermentation that has been improved to a significant extent. With the use of such mutant yeast strain, accordingly, ethanol productivity can be improved.

EXAMPLES

Hereafter, the present invention is described in greater detail with reference to the examples, although the technical scope of the present invention is not limited to these examples.

[Method for Producing Xylose-Assimilating Yeast Strain]

In accordance with the method disclosed in JP 2014-193152 A, a yeast strain Uz736 having xylose-metabolizing ability was prepared. The detail is described below.

At the outset, uracil auxotrophic strains (OC2-U) of the homothallic wine yeast *Saccharomyces cerevisiae* OC2 strain were obtained via UV-induced mutation. While disrupting the ribosomal RNA gene locus, the HIS3 gene locus, the LEU2 gene locus, the TRP1 gene locus, and the GRE3 gene locus of the OC2-U strain, a xylose isomerase (XI) gene derived from the intestinal protozoa of *Reticulitermes speratus*, a yeast-derived TAL1 gene, a yeast-derived TKL1 gene, a yeast-derived PRE1 gene, a yeast-derived RKI1 gene, and a yeast-derived XKS1 gene were introduced thereinto with the use of marker genes (i.e., hygromycin-resistant gene, HIS3 gene, LEU2 gene, URA3 gene, and TRP1 gene) to produce the OC700 strain. While disrupting the ADH2 gene, the *E. coli*-derived acetaldehyde dehydrogenase (mhpF) gene and a yeast-derived ADH1 gene were introduced into the ADH2 gene locus of the OC700 strain. Thus, the Uz736 strain was produced.

[Method for Breeding Xylose-Assimilating Yeast Strain]

Subsequently, the Uz736 strain was subjected to long-term culture to breed yeast strains with improved ethanol fermentation ability. At the outset, the Uz736 strain was subjected to long-term culture for 30 to 60 days in a liquid medium prepared by biomass saccharification. The cultured yeast was inoculated into a YPD agar medium (10 g/l dry yeast extract, 20 g/l bactopeptone, 20 g/l glucose, and 20 g/l agar) to obtain single colonies. The ethanol fermentation ability of the single colonies was evaluated to obtain a breeding yeast with improved ethanol fermentation ability.

Specifically, the single colonies were inoculated into a YPD agar medium (10 g/l yeast extract, 20 g/l peptone, and 20 g/l glucose) and subjected to shake culture (80 rpm, amplitude 35 mm, 30° C.) or stationary culture at 30° C. for 24 hours. Thereafter, the single colonies were separately inoculated into various media for ethanol production of different components and then subjected to shake culture (80 rpm, amplitude 35 mm, 30° C.) or stationary culture in an incubator at 31° C. to perform the fermentation test. The inside of the reaction vessel was maintained in the anaerobic condition.

Ethanol in a fermentation liquor was assayed using a biosensor (BF-5, Oji Scientific Instruments) or via HPLC (LC-10A, Shimadzu Corporation) under the conditions described below.

[Biosensor]
Temperature: 37° C.
Flow rate: 0.8 ml/min
[HPLC]
Column: AminexHPX-87H
Mobile phase: 0.01 N $H_2SO_4$
Flow rate: 0.6 ml/min
Temperature: 30° C.
Detector: Differential refractometer (RID-10A)

Subsequently, yeast strains with the improved fermentation ability were cultured in a sporulation medium at 25° C. for 5 days and then recovered. The recovered yeast strains were treated with a 1 ml of a reaction solution comprising 125 U of zymolyase in 50 mM phosphate buffer (pH 7.5) for 2 hours for cell wall lysis. Thereafter, Tween 80 was added to a concentration of 1% therein, the resultant was vigorously stirred to separate spores from each other, and the separated spores were inoculated in an agar medium to form single colonies. The yeast single colonies were repeatedly subjected to long-term culture to formation of single colonies. Thus, 4 types of breeding strains; i.e., Uz1015, Uz1229, Uz1230, and Uz1235, with the improved ethanol fermentation ability were obtained.

[Method of Mutation Analysis]

OC700 and Uz736 used in the example and Uz1015, Uz1229, Uz1230, and Uz1235 produced in the example were subjected to next-generation sequence analysis (Hiseq) (Takara Bio Inc.). The obtained sequence data were analyzed in terms of the sites of mutation using analytical software (NextGENe, SoftGenetics). The gene sequence data of *Saccharomyces cerevisiae* S288C were used for reference, and default settings of analytical parameters were employed. The obtained data of mutations were compared, and 6 types of gene mutations that were common between Uz1230 and Uz1235 with excellent ethanol fermentation ability and were not present in other 4 types of genes were identified.

Specifically, a mutation causing substitution of leucine 324 with cysteine in the CDC123 gene (L324C), G704E in the FPK1 gene, S112T in the SUI3 gene, V195* in the YPR1 gene, G599D in the EPO1 gene, and G328E in the YPL150w gene were identified.

[Method of Producing Mutant Yeast]

In the same manner as with the case of the Uz736 strain described above, a xylose isomerase (XI) gene derived from the intestinal protozoa of *Reticulitermes speratus* and a yeast-derived XKS1 gene were introduced into the laboratory yeast strain *Saccharomyces cerevisiae* BY4742 with the use of the marker genes (i.e., hygromycin-resistant gene and URA3d gene) while disrupting the ribosomal RNA gene locus and the GRE3 gene locus thereof. Thus, the Uz2443 strain having xylose-metabolizing ability was produced. Six types of plasmids necessary for introduction of mutations into the CDC123 gene, the FPK1 gene, the SUI3 gene, the YPR1 gene, the EPO1 gene, and the YPL150w gene of the Uz2443 strain were prepared.

Specifically, the genome of the Uz1230 strain as a template was amplified via PCR, so that the resultant would comprise an upstream 500-bp region and a downstream 500-bp region of ORF of the relevant mutant gene.

More specifically, the genome of the Uz2443 strain as a template was amplified with the use of the primers shown in Table 4. Thus, the CDC123 gene, the FPK1 gene, the SUI3 gene, the YPR1 gene, the EPO1 gene, and the YPL150w gene into which mutations had been introduced were amplified. The amplified fragments were cloned into vectors comprising hygromycin-resistant genes to prepare 6 types of vectors.

TABLE 4

| Primer name | Sequence | SEQ ID NO: |
|---|---|---|
| V_CDC123 INF | CTGACTTGAGCGTCGAAGATTACAAG CAAGTATTAGTAGCCTC | 51 |
| V_CDC123 INR | CTATACAGCGGAATTCCCATTTGAAA TGGTTTGAAAATGAATT | 52 |
| V_FPK1 INF | CTGACTTGAGCGTCGCCATCTTCGAT CCAGGAGCTCACCGATG | 53 |
| V_FPK1 INR | CTATACAGCGGAATTGCCGGTTTCCT GGATTTTTGAGCATTTTGC | 54 |
| V_SUI3 INF | CTGACTTGAGCGTCGGTGACTTGTTC AATTTCTGTACCCTTTG | 55 |
| V_SUI3 INR | CTATACAGCGGAATTGATATTTGGTC TTTGGGTTGTACGTTCT | 56 |
| V_YMR124w INF | CTGACTTGAGCGTCGTGCCCTCCTAA TTTTTTTTTTTTTTAGT | 57 |
| V_YMR124w INR | CTATACAGCGGAATTATAATCCTAGG AATGTAAAACAAAGTAA | 58 |
| V_YPL150w INF | CTGACTTGAGCGTCGTGAGCACCCTT ACTTAATAAAAGAGTTG | 59 |
| V_YPL150w INR | CTATACAGCGGAATTGACTTCCTTTC ATCAAAAATGAAGGATC | 60 |
| V_YRP1 INF | CTGACTTGAGCGTCGGACTATTTTAA TTACGTTGGTGTCATTG | 61 |
| V_YRP1 INR | CTATACAGCGGAATTAGATTCGTTTT CTTTTTCTCGTTGTTCA | 62 |

In order to knock out the CDC123 gene, the FPK1 gene, the SUI3 gene, the YPR1 gene, the EPO1 gene, and the YPL150w gene endogenous in the Uz2443 strain and separately introduce the mutant CDC123, FPK1, SUI3, YPR1, EPO1, and YPL150w genes into the Uz2443 strain, PCR was carried out with the use of the primers shown in Table 5 and the prepared vectors as templates. The 6 types of vectors were linearized. The linearized vectors were each transformed into the Uz2443 strain, and yeast strains grown on a hygromycin-containing selection medium were subjected to screening. As a result, 6 types of mutant yeast strains were obtained by introducing the relevant mutations into the Uz2443 strain.

TABLE 5

| Primer name | Sequence | SEQ ID NO: |
| --- | --- | --- |
| CDC123d_F | ATACCAGTGACAAGAGAGCAGGTTGAACAC | 63 |
| CDC123_R | GTCTATAAAAGTTGTTTATTCTTGTGAGG | 64 |
| FPK1d_F | CGACCACGAGCAAGAACACGAACACGATTC | 65 |
| FPK1_R | CGCTCTTATTCATGTTCGTGATGGTGTCC | 66 |
| SUI3d_F | CTACACTAAAGAAGAAAAAGAAGACTAAAA | 67 |
| SUI3_R | GGTCGAATCCTAACTAAGCAGCTAAATCGG | 68 |
| YMR124wd_F | TAAGCAATAATCGCGATAATGTTAATGGTA | 69 |
| YMR124w_R | GTGATGGTTAGGTGAAGTTATGCTGCATG | 70 |
| YPL150wd_F | AATATAAAAAGCATTATAGGATCATCGTAC | 71 |
| YPL150w_R | GTTTTGTTCCAATTACGAAGATCCAACAGG | 72 |
| YPR1d_F | TACATTAAAACTAAATACTGGTGCCTCCAT | 73 |
| YPR1_R | GCAGAAGAATTCTTTTACGTAGCAGGCATG | 74 |

[Evaluation of Mutant Gene]

One platinum loopful each of 6 types of mutant yeast strains having the xylose-metabolizing ability each comprising a relevant mutant gene among the 6 types of the mutant genes and a yeast strain having xylose-metabolizing ability into which no mutation had been introduced was fractionated from an agar medium and subjected to shake culture in a triangular flask containing 8 ml of YPD medium (10 g/l dry yeast extract, 20 g/l bactopeptone, and 20 g/l glucose) at 32° C. and 150 rpm for 24 hours. Thereafter, the initial PCVs of the yeast strains were adjusted to 0.12 and subjected to shake culture in 8 ml of the medium (80 g/l glucose, 100 g/l xylose, 0.3 g/l vanillin, 0.2 g/l syringaldehyde, 10 g/l acetic acid, 0.8 g/l furfural, and 10 g/l dry yeast extract) at 35° C. and 80 rpm for 90 hours.

After the completion of culture, ethanol concentration was analyzed via HPLC (column: AminexHPX-87H; mobile phase: 0.01 N $H_2SO_4$; flow rate: 0.6 ml/min; temperature: 30° C.; detector: differential refractometer RID-10A). The results are shown in FIG. 1. As shown in FIG. 1, L324C in the CDC123 gene, G704E in the FPK1 gene, and S112T in the SUI3 gene among the 6 type of mutant genes were found to improve the ethanol fermentation ability. In contrast, it was found that other mutant genes identified in the example would not improve or would slightly improve the ethanol fermentation ability. Thus, L324C in the CDC123 gene, G704E in the FPK1 gene, and S112T in the SUI3 gene were found to be excellent mutations to achieve the improved ethanol fermentation ability.

All publications, patents, and patent applications cited herein are incorporated herein by reference in their entirety.

The invention claimed is:

1. A mutant gene encoding a mutant FPK1 (serine/threonine protein kinase) protein, wherein said mutant FPK1 protein comprises:

(a) the amino acid sequence of SEQ ID NO: 9; or (b) an amino acid sequence having 95% or higher identity to the amino acid sequence of SEQ ID NO: 9 in which an amino acid residue corresponding to the 704th position from the N terminus of the amino acid sequence of SEQ ID NO: 9 is glutamic acid.

2. A mutant yeast strain having xylose-metabolizing ability, which comprises the mutant gene according to claim 1.

3. A method for producing ethanol comprising a step of culturing the mutant yeast strain according to claim 2 in a xylose-containing medium and performing ethanol fermentation.

4. The method for producing ethanol according to claim 3, wherein the medium contains cellulose and the ethanol fermentation proceeds simultaneously at least with the cellulose saccharification.

* * * * *

SEQUENCE LISTING

```
<160> NUMBER OF SEQ ID NOS: 74

<210> SEQ ID NO 1
<211> LENGTH: 34
<212> TYPE: PRT
<213> ORGANISM: Artificial Sequence
<220> FEATURE:
<223> OTHER INFORMATION: Synthetic sequence, consensus sequence of
      CDC123
<220> FEATURE:
<221> NAME/KEY: misc_feature
<222> LOCATION: (1)..(1)
<223> OTHER INFORMATION: Xaa = Glu, Arg, Gln, Lys or Asp
<220> FEATURE:
<221> NAME/KEY: misc_feature
<222> LOCATION: (5)..(5)
<223> OTHER INFORMATION: Xaa = Leu or Phe
<220> FEATURE:
<221> NAME/KEY: misc_feature
<222> LOCATION: (7)..(7)
<223> OTHER INFORMATION: Xaa = Leu or Ile
<220> FEATURE:
<221> NAME/KEY: misc_feature
<222> LOCATION: (8)..(8)
<223> OTHER INFORMATION: Xaa = Val, Ile or Leu
<220> FEATURE:
<221> NAME/KEY: misc_feature
<222> LOCATION: (9)..(9)
<223> OTHER INFORMATION: Xaa = Thr, Lys, Pro or Leu
<220> FEATURE:
<221> NAME/KEY: misc_feature
<222> LOCATION: (10)..(10)
<223> OTHER INFORMATION: Xaa = Arg, Ser or Glu
<220> FEATURE:
<221> NAME/KEY: misc_feature
<222> LOCATION: (11)..(11)
<223> OTHER INFORMATION: Xaa = His, Asn or Thr
<220> FEATURE:
<221> NAME/KEY: misc_feature
<222> LOCATION: (13)..(13)
<223> OTHER INFORMATION: Xaa = Thr, Ile or Val
<220> FEATURE:
```

-continued

```
<221> NAME/KEY: misc_feature
<222> LOCATION: (14)..(14)
<223> OTHER INFORMATION: Xaa = Gly, Cys or Ala
<220> FEATURE:
<221> NAME/KEY: misc_feature
<222> LOCATION: (17)..(17)
<223> OTHER INFORMATION: Xaa = Ala or Val
<220> FEATURE:
<221> NAME/KEY: misc_feature
<222> LOCATION: (18)..(18)
<223> OTHER INFORMATION: Xaa = Ser, Thr, His or Cys
<220> FEATURE:
<221> NAME/KEY: misc_feature
<222> LOCATION: (23)..(23)
<223> OTHER INFORMATION: Xaa = Glu or Gln
<220> FEATURE:
<221> NAME/KEY: misc_feature
<222> LOCATION: (25)..(25)
<223> OTHER INFORMATION: Xaa = His or Gln
<220> FEATURE:
<221> NAME/KEY: misc_feature
<222> LOCATION: (28)..(28)
<223> OTHER INFORMATION: Xaa = Gln, Lys, Arg, Ile or Thr
<220> FEATURE:
<221> NAME/KEY: misc_feature
<222> LOCATION: (30)..(30)
<223> OTHER INFORMATION: Xaa = Leu, Val or Ile
<220> FEATURE:
<221> NAME/KEY: misc_feature
<222> LOCATION: (31)..(31)
<223> OTHER INFORMATION: Xaa = Leu, Val or Ile
<220> FEATURE:
<221> NAME/KEY: misc_feature
<222> LOCATION: (32)..(32)
<223> OTHER INFORMATION: Xaa = Glu or Asp
<220> FEATURE:
<221> NAME/KEY: misc_feature
<222> LOCATION: (34)..(34)
<223> OTHER INFORMATION: Xaa = Ser, Ala or Thr

<400> SEQUENCE: 1

Xaa Asp Tyr Glu Xaa Arg Xaa Xaa Xaa Xaa Asn Xaa Xaa Arg Phe
 1               5                  10                  15

Xaa Xaa Lys Glu His Ser Xaa Asn Xaa Val Pro Xaa Asp Xaa Xaa
             20                  25                  30

Ala Xaa

<210> SEQ ID NO 2
<211> LENGTH: 1083
<212> TYPE: DNA
<213> ORGANISM: Saccharomyces cerevisiae
<220> FEATURE:
<221> NAME/KEY: CDS
<222> LOCATION: (1)..(1083)

<400> SEQUENCE: 2 atg tcc tca caa gaa tat aca act ttt ata gac ata cca gtg aca aga      48
Met Ser Ser Gln Glu Tyr Thr Thr Phe Ile Asp Ile Pro Val Thr Arg
 1               5                  10                  15 gag cag gtt gaa cac tgt tct tac tcg ttt tgg tcc tcg ctg tat ccc      96
Glu Gln Val Glu His Cys Ser Tyr Ser Phe Trp Ser Ser Leu Tyr Pro
             20                  25                  30 aaa tat gtg ccg aaa tcc ata gtg tta aaa tcc tta ccg aaa aaa ttt     144
Lys Tyr Val Pro Lys Ser Ile Val Leu Lys Ser Leu Pro Lys Lys Phe
         35                  40                  45 att caa tat ttg gaa caa gac ggt atc aag cta ccc caa gag gaa aac     192
Ile Gln Tyr Leu Glu Gln Asp Gly Ile Lys Leu Pro Gln Glu Glu Asn
     50                  55                  60 tcc agg tct gtg tac acc gag gaa ata ata aga aat gaa gat aat gac     240
Ser Arg Ser Val Tyr Thr Glu Glu Ile Ile Arg Asn Glu Asp Asn Asp
```

```
                    65                  70                  75                  80 tat agt gat tgg gag gac gat gag gat acc gcc acc gaa ttt gtc caa      288
Tyr Ser Asp Trp Glu Asp Asp Glu Asp Thr Ala Thr Glu Phe Val Gln
                85                  90                  95 gaa gtt gag cca ttg ata gat ttt cca gaa tta cac cag aaa tta aag      336
Glu Val Glu Pro Leu Ile Asp Phe Pro Glu Leu His Gln Lys Leu Lys
            100                 105                 110 gat gct ttg aac gaa tta ggt gca gtg gct ccc aag tta aac tgg tct      384
Asp Ala Leu Asn Glu Leu Gly Ala Val Ala Pro Lys Leu Asn Trp Ser
        115                 120                 125 gca cca aga gac gct acc tgg att ttg ccg aat aac act atg aag tgt      432
Ala Pro Arg Asp Ala Thr Trp Ile Leu Pro Asn Asn Thr Met Lys Cys
    130                 135                 140 aac gag gta aat gaa ctt tac cta ttg ttg aac gca tcc aat tat ata      480
Asn Glu Val Asn Glu Leu Tyr Leu Leu Leu Asn Ala Ser Asn Tyr Ile
145                 150                 155                 160 atg cat gac ctt caa aga gca ttt aaa ggc tgc gtg gac ggg gat gat      528
Met His Asp Leu Gln Arg Ala Phe Lys Gly Cys Val Asp Gly Asp Asp
                165                 170                 175 ata aaa gga ttg aaa ttt gac ttg gta ctt aga caa tgg tgt gat atg      576
Ile Lys Gly Leu Lys Phe Asp Leu Val Leu Arg Gln Trp Cys Asp Met
            180                 185                 190 aat ccg gca ctc gaa ttt agg gtc ttc gtt aag aat gcg cat atc gtt      624
Asn Pro Ala Leu Glu Phe Arg Val Phe Val Lys Asn Ala His Ile Val
        195                 200                 205 ggg gcc acc cag cgt gat tta aat tat tat gac tat tta gat gag ttg      672
Gly Ala Thr Gln Arg Asp Leu Asn Tyr Tyr Asp Tyr Leu Asp Glu Leu
    210                 215                 220 tca gat acc ttc aag gac ctt att gat gaa ata gtt cat gat gtc gtc      720
Ser Asp Thr Phe Lys Asp Leu Ile Asp Glu Ile Val His Asp Val Val
225                 230                 235                 240 ctg ccc aag ttt cct gat aaa agt ttc gtt ctt gac gtt tat att cca      768
Leu Pro Lys Phe Pro Asp Lys Ser Phe Val Leu Asp Val Tyr Ile Pro
                245                 250                 255 aga cct ttc aat aaa atc ttc att gtt gat ata aat ccg ttt gcc agg      816
Arg Pro Phe Asn Lys Ile Phe Ile Val Asp Ile Asn Pro Phe Ala Arg
            260                 265                 270 aag aca gat tct ttg cta ttt tca tgg aac gag att gct gcg ata gca      864
Lys Thr Asp Ser Leu Leu Phe Ser Trp Asn Glu Ile Ala Ala Ile Ala
        275                 280                 285 cct ccg aag aat gat gtt gaa gat tat gaa tta agg tta gtg acg agg      912
Pro Pro Lys Asn Asp Val Glu Asp Tyr Glu Leu Arg Leu Val Thr Arg
    290                 295                 300 cat aac acg ggg aga ttc gct tca aaa gag cat tcc gaa aat cat gtt      960
His Asn Thr Gly Arg Phe Ala Ser Lys Glu His Ser Glu Asn His Val
305                 310                 315                 320 cca cag gat tgc gta gaa gct agt tta aat cct gaa gca atc cga gag     1008
Pro Gln Asp Cys Val Glu Ala Ser Leu Asn Pro Glu Ala Ile Arg Glu
                325                 330                 335 ctc act caa aaa tgg aaa gaa cta ctc tct caa cag gca aag gaa gaa     1056
Leu Thr Gln Lys Trp Lys Glu Leu Leu Ser Gln Gln Ala Lys Glu Glu
            340                 345                 350 agc agt gat agt gag agt gaa act tag                                 1083
Ser Ser Asp Ser Glu Ser Glu Thr
        355                 360

<210> SEQ ID NO 3
<211> LENGTH: 360
<212> TYPE: PRT
<213> ORGANISM: Saccharomyces cerevisiae
```

<400> SEQUENCE: 3

```
Met Ser Ser Gln Glu Tyr Thr Thr Phe Ile Asp Ile Pro Val Thr Arg
1               5                   10                  15
Glu Gln Val Glu His Cys Ser Tyr Ser Phe Trp Ser Ser Leu Tyr Pro
            20                  25                  30
Lys Tyr Val Pro Lys Ser Ile Val Leu Lys Ser Leu Pro Lys Lys Phe
        35                  40                  45
Ile Gln Tyr Leu Glu Gln Asp Gly Ile Lys Leu Pro Gln Glu Glu Asn
    50                  55                  60
Ser Arg Ser Val Tyr Thr Glu Glu Ile Ile Arg Asn Glu Asp Asn Asp
65                  70                  75                  80
Tyr Ser Asp Trp Glu Asp Glu Asp Thr Ala Thr Glu Phe Val Gln
                85                  90                  95
Glu Val Glu Pro Leu Ile Asp Phe Pro Glu Leu His Gln Lys Leu Lys
            100                 105                 110
Asp Ala Leu Asn Glu Leu Gly Ala Val Ala Pro Lys Leu Asn Trp Ser
        115                 120                 125
Ala Pro Arg Asp Ala Thr Trp Ile Leu Pro Asn Asn Thr Met Lys Cys
    130                 135                 140
Asn Glu Val Asn Glu Leu Tyr Leu Leu Leu Asn Ala Ser Asn Tyr Ile
145                 150                 155                 160
Met His Asp Leu Gln Arg Ala Phe Lys Gly Cys Val Asp Gly Asp Asp
                165                 170                 175
Ile Lys Gly Leu Lys Phe Asp Leu Val Leu Arg Gln Trp Cys Asp Met
            180                 185                 190
Asn Pro Ala Leu Glu Phe Arg Val Phe Val Lys Asn Ala His Ile Val
        195                 200                 205
Gly Ala Thr Gln Arg Asp Leu Asn Tyr Tyr Asp Tyr Leu Asp Glu Leu
    210                 215                 220
Ser Asp Thr Phe Lys Asp Leu Ile Asp Glu Ile Val His Asp Val Val
225                 230                 235                 240
Leu Pro Lys Phe Pro Asp Lys Ser Phe Val Leu Asp Val Tyr Ile Pro
                245                 250                 255
Arg Pro Phe Asn Lys Ile Phe Ile Val Asp Ile Asn Pro Phe Ala Arg
            260                 265                 270
Lys Thr Asp Ser Leu Leu Phe Ser Trp Asn Glu Ile Ala Ala Ile Ala
        275                 280                 285
Pro Pro Lys Asn Asp Val Glu Asp Tyr Glu Leu Arg Leu Val Thr Arg
    290                 295                 300
His Asn Thr Gly Arg Phe Ala Ser Lys Glu His Ser Glu Asn His Val
305                 310                 315                 320
Pro Gln Asp Cys Val Glu Ala Ser Leu Asn Pro Glu Ala Ile Arg Glu
                325                 330                 335
Leu Thr Gln Lys Trp Lys Glu Leu Leu Ser Gln Ala Lys Glu Glu
            340                 345                 350
Ser Ser Asp Ser Glu Ser Glu Thr
        355                 360
```

<210> SEQ ID NO 4
<211> LENGTH: 48
<212> TYPE: PRT
<213> ORGANISM: Artificial Sequence
<220> FEATURE:
<223> OTHER INFORMATION: Synthetic sequence, consensus sequence of SUI3

```
<220> FEATURE:
<221> NAME/KEY: misc_feature
<222> LOCATION: (2)..(2)
<223> OTHER INFORMATION: Xaa = Asp or Glu
<220> FEATURE:
<221> NAME/KEY: misc_feature
<222> LOCATION: (3)..(3)
<223> OTHER INFORMATION: Xaa = Ile, Val, Leu or Ala
<220> FEATURE:
<221> NAME/KEY: misc_feature
<222> LOCATION: (4)..(4)
<223> OTHER INFORMATION: Xaa = Ala, Thr or Ser
<220> FEATURE:
<221> NAME/KEY: misc_feature
<222> LOCATION: (5)..(5)
<223> OTHER INFORMATION: Xaa = Glu or Asp
<220> FEATURE:
<221> NAME/KEY: misc_feature
<222> LOCATION: (6)..(6)
<223> OTHER INFORMATION: Xaa = Ala or Val
<220> FEATURE:
<221> NAME/KEY: misc_feature
<222> LOCATION: (7)..(7)
<223> OTHER INFORMATION: Xaa = Leu or Phe
<220> FEATURE:
<221> NAME/KEY: misc_feature
<222> LOCATION: (9)..(9)
<223> OTHER INFORMATION: Xaa = Glu or Leu
<220> FEATURE:
<221> NAME/KEY: misc_feature
<222> LOCATION: (11)..(11)
<223> OTHER INFORMATION: Xaa = Ser, Thr or Lys
<220> FEATURE:
<221> NAME/KEY: misc_feature
<222> LOCATION: (19)..(19)
<223> OTHER INFORMATION: Xaa = Thr, Ser or Ala
<220> FEATURE:
<221> NAME/KEY: misc_feature
<222> LOCATION: (20)..(20)
<223> OTHER INFORMATION: Xaa = Lys, Ala or Pro
<220> FEATURE:
<221> NAME/KEY: misc_feature
<222> LOCATION: (21)..(21)
<223> OTHER INFORMATION: Xaa = Asp, His, Glu or Val
<220> FEATURE:
<221> NAME/KEY: misc_feature
<222> LOCATION: (22)..(22)
<223> OTHER INFORMATION: Xaa = Ser, Val, Thr or Ala
<220> FEATURE:
<221> NAME/KEY: misc_feature
<222> LOCATION: (23)..(23)
<223> OTHER INFORMATION: Xaa = Ser, Ala, Thr, Asp, Glu or Asn
<220> FEATURE:
<221> NAME/KEY: misc_feature
<222> LOCATION: (24)..(24)
<223> OTHER INFORMATION: Xaa = Val or Leu
<220> FEATURE:
<221> NAME/KEY: misc_feature
<222> LOCATION: (26)..(26)
<223> OTHER INFORMATION: Xaa = Ala, Asp or Glu
<220> FEATURE:
<221> NAME/KEY: misc_feature
<222> LOCATION: (29)..(29)
<223> OTHER INFORMATION: Xaa = Lys or Gln
<220> FEATURE:
<221> NAME/KEY: misc_feature
<222> LOCATION: (30)..(30)
<223> OTHER INFORMATION: Xaa = Glu or Gln
<220> FEATURE:
<221> NAME/KEY: misc_feature
<222> LOCATION: (33)..(33)
<223> OTHER INFORMATION: Xaa = Lys, Arg or Ser
<220> FEATURE:
<221> NAME/KEY: misc_feature
<222> LOCATION: (36)..(36)
<223> OTHER INFORMATION: Xaa = Leu or Val
<220> FEATURE:
<221> NAME/KEY: misc_feature
<222> LOCATION: (37)..(37)
```

```
<223> OTHER INFORMATION: Xaa = Asp, Asn or Lys
<220> FEATURE:
<221> NAME/KEY: misc_feature
<222> LOCATION: (38)..(38)
<223> OTHER INFORMATION: Xaa = Asn, Ser or Val
<220> FEATURE:
<221> NAME/KEY: misc_feature
<222> LOCATION: (39)..(39)
<223> OTHER INFORMATION: Xaa = Val, Ile, Asp or Ala
<220> FEATURE:
<221> NAME/KEY: misc_feature
<222> LOCATION: (40)..(40)
<223> OTHER INFORMATION: Xaa = Asp, Glu, Thr, Ser, Gly or Val
<220> FEATURE:
<221> NAME/KEY: misc_feature
<222> LOCATION: (41)..(41)
<223> OTHER INFORMATION: Xaa = Ala, Gly, Ser, Glu, Thr, Ala, Asp or Val
<220> FEATURE:
<221> NAME/KEY: misc_feature
<222> LOCATION: (42)..(42)
<223> OTHER INFORMATION: Xaa = Glu, Asn or Asp
<220> FEATURE:
<221> NAME/KEY: misc_feature
<222> LOCATION: (43)..(43)
<223> OTHER INFORMATION: Xaa = Ser or Asn
<220> FEATURE:
<221> NAME/KEY: misc_feature
<222> LOCATION: (44)..(44)
<223> OTHER INFORMATION: Xaa = Lys, Ser, Gln or Asn
<220> FEATURE:
<221> NAME/KEY: misc_feature
<222> LOCATION: (45)..(45)
<223> OTHER INFORMATION: Xaa = Glu, Lys or Asp
<220> FEATURE:
<221> NAME/KEY: misc_feature
<222> LOCATION: (46)..(46)
<223> OTHER INFORMATION: Xaa = Gly, Ala, Thr, Asp, Ser or Glu
<220> FEATURE:
<221> NAME/KEY: misc_feature
<222> LOCATION: (47)..(47)
<223> OTHER INFORMATION: Xaa = Thr or Ser
<220> FEATURE:
<221> NAME/KEY: misc_feature
<222> LOCATION: (48)..(48)
<223> OTHER INFORMATION: Xaa = Pro or Thr

<400> SEQUENCE: 4

Asp Xaa Xaa Xaa Xaa Xaa Xaa Gly Xaa Leu Xaa Leu Lys Lys Lys Lys
1               5                   10                  15

Lys Lys Xaa Xaa Xaa Xaa Xaa Xaa Asp Xaa Phe Glu Xaa Xaa Leu Ala
            20                  25                  30

Xaa Ala Gly Xaa Xaa Xaa Xaa Xaa Xaa Xaa Xaa Xaa Xaa Xaa Xaa Xaa
        35                  40                  45

<210> SEQ ID NO 5
<211> LENGTH: 858
<212> TYPE: DNA
<213> ORGANISM: Saccharomyces cerevisiae
<220> FEATURE:
<221> NAME/KEY: CDS
<222> LOCATION: (1)..(858)

<400> SEQUENCE: 5 atg tcc tcc gat tta gct gct gag tta gga ttc gac cct aca cta aag    48
Met Ser Ser Asp Leu Ala Ala Glu Leu Gly Phe Asp Pro Thr Leu Lys
1               5                   10                  15 aag aaa aag aag act aaa aag gtg atc cca gat gat ttt gat gct gcc    96
Lys Lys Lys Lys Thr Lys Lys Val Ile Pro Asp Asp Phe Asp Ala Ala
            20                  25                  30 gta aac ggc aaa gaa aat ggt tca gga gat gat tta ttt gcc gga tta   144
Val Asn Gly Lys Glu Asn Gly Ser Gly Asp Asp Leu Phe Ala Gly Leu
        35                  40                  45
```

```
aaa aag aaa aag aag aag tcc aag agc gtt tct gcc gat gct gaa gct    192
Lys Lys Lys Lys Lys Lys Ser Lys Ser Val Ser Ala Asp Ala Glu Ala
 50                  55                  60 gaa aaa gag cct act gac gac ata gca gaa gcc ttg ggt gaa cta tcc    240
Glu Lys Glu Pro Thr Asp Asp Ile Ala Glu Ala Leu Gly Glu Leu Ser
 65                  70                  75                  80 ttg aag aag aaa aag aaa aag aca aag gac agc agt gta gac gcg ttt    288
Leu Lys Lys Lys Lys Lys Lys Thr Lys Asp Ser Ser Val Asp Ala Phe
                 85                  90                  95 gag aaa gaa cta gct aaa gct ggt cta gat aat gtg gat gct gaa acc    336
Glu Lys Glu Leu Ala Lys Ala Gly Leu Asp Asn Val Asp Ala Glu Thr
            100                 105                 110 aaa gaa ggc act cca agt gct aat tcc agc att caa caa gaa gtt ggc    384
Lys Glu Gly Thr Pro Ser Ala Asn Ser Ser Ile Gln Gln Glu Val Gly
        115                 120                 125 cta cct tat tca gag tta tta tct aga ttt ttc aat att cta aga act    432
Leu Pro Tyr Ser Glu Leu Leu Ser Arg Phe Phe Asn Ile Leu Arg Thr
130                 135                 140 aac aat cca gaa ctt gct ggt gat aga agt ggt cca aag ttc aga att    480
Asn Asn Pro Glu Leu Ala Gly Asp Arg Ser Gly Pro Lys Phe Arg Ile
145                 150                 155                 160 cct cct cct gtt tgt ttg cgt gat ggt aag aag act att ttc tcg aat    528
Pro Pro Pro Val Cys Leu Arg Asp Gly Lys Lys Thr Ile Phe Ser Asn
                165                 170                 175 atc caa gat atc gcc gaa aaa ttg cat aga tct ccg gaa cat ttg att    576
Ile Gln Asp Ile Ala Glu Lys Leu His Arg Ser Pro Glu His Leu Ile
            180                 185                 190 caa tat ctc ttc gca gaa tta ggt acg tcc ggt tct gtt gac ggt cag    624
Gln Tyr Leu Phe Ala Glu Leu Gly Thr Ser Gly Ser Val Asp Gly Gln
        195                 200                 205 aaa aga tta gtc att aag ggt aag ttt caa tcc aaa caa atg gag aat    672
Lys Arg Leu Val Ile Lys Gly Lys Phe Gln Ser Lys Gln Met Glu Asn
210                 215                 220 gtc tta aga aga tac att ttg gag tat gtc act tgt aaa act tgt aag    720
Val Leu Arg Arg Tyr Ile Leu Glu Tyr Val Thr Cys Lys Thr Cys Lys
225                 230                 235                 240 agt att aac acc gaa ttg aag aga gaa cag tca aac aga ctg ttc ttt    768
Ser Ile Asn Thr Glu Leu Lys Arg Glu Gln Ser Asn Arg Leu Phe Phe
                245                 250                 255 atg gtc tgt aaa agt tgt ggt tct acc aga tcc gtc tct tct att aaa    816
Met Val Cys Lys Ser Cys Gly Ser Thr Arg Ser Val Ser Ser Ile Lys
            260                 265                 270 acc ggt ttc caa gct acc gtt ggt aag aga agg aga atg tga            858
Thr Gly Phe Gln Ala Thr Val Gly Lys Arg Arg Arg Met
        275                 280                 285

<210> SEQ ID NO 6
<211> LENGTH: 285
<212> TYPE: PRT
<213> ORGANISM: Saccharomyces cerevisiae

<400> SEQUENCE: 6

Met Ser Ser Asp Leu Ala Ala Glu Leu Gly Phe Asp Pro Thr Leu Lys
 1               5                  10                  15

Lys Lys Lys Lys Thr Lys Lys Val Ile Pro Asp Asp Phe Asp Ala Ala
                20                  25                  30

Val Asn Gly Lys Glu Asn Gly Ser Gly Asp Asp Leu Phe Ala Gly Leu
            35                  40                  45

Lys Lys Lys Lys Lys Lys Ser Lys Ser Val Ser Ala Asp Ala Glu Ala
```

```
                50                  55                  60
Glu Lys Glu Pro Thr Asp Asp Ile Ala Glu Ala Leu Gly Glu Leu Ser
65                  70                  75                  80

Leu Lys Lys Lys Lys Lys Thr Lys Asp Ser Ser Val Asp Ala Phe
                85                  90                  95

Glu Lys Glu Leu Ala Lys Ala Gly Leu Asp Asn Val Asp Ala Glu Thr
            100                 105                 110

Lys Glu Gly Thr Pro Ser Ala Asn Ser Ser Ile Gln Gln Glu Val Gly
        115                 120                 125

Leu Pro Tyr Ser Glu Leu Leu Ser Arg Phe Phe Asn Ile Leu Arg Thr
    130                 135                 140

Asn Asn Pro Glu Leu Ala Gly Asp Arg Ser Gly Pro Lys Phe Arg Ile
145                 150                 155                 160

Pro Pro Pro Val Cys Leu Arg Asp Gly Lys Lys Thr Ile Phe Ser Asn
                165                 170                 175

Ile Gln Asp Ile Ala Glu Lys Leu His Arg Ser Pro Glu His Leu Ile
            180                 185                 190

Gln Tyr Leu Phe Ala Glu Leu Gly Thr Ser Gly Ser Val Asp Gly Gln
        195                 200                 205

Lys Arg Leu Val Ile Lys Gly Lys Phe Gln Ser Lys Gln Met Glu Asn
    210                 215                 220

Val Leu Arg Arg Tyr Ile Leu Glu Tyr Val Thr Cys Lys Thr Cys Lys
225                 230                 235                 240

Ser Ile Asn Thr Glu Leu Lys Arg Glu Gln Ser Asn Arg Leu Phe Phe
                245                 250                 255

Met Val Cys Lys Ser Cys Gly Ser Thr Arg Ser Val Ser Ser Ile Lys
            260                 265                 270

Thr Gly Phe Gln Ala Thr Val Gly Lys Arg Arg Met
        275                 280                 285

<210> SEQ ID NO 7
<211> LENGTH: 80
<212> TYPE: PRT
<213> ORGANISM: Artificial Sequence
<220> FEATURE:
<223> OTHER INFORMATION: Synthetic sequence, consensus sequence of FPK1
<220> FEATURE:
<221> NAME/KEY: misc_feature
<222> LOCATION: (41)..(41)
<223> OTHER INFORMATION: Xaa = Phe or Ile
<220> FEATURE:
<221> NAME/KEY: misc_feature
<222> LOCATION: (46)..(46)
<223> OTHER INFORMATION: Xaa = Gly or Ala
<220> FEATURE:
<221> NAME/KEY: misc_feature
<222> LOCATION: (47)..(47)
<223> OTHER INFORMATION: Xaa = Asp, Glu or Ser
<220> FEATURE:
<221> NAME/KEY: misc_feature
<222> LOCATION: (48)..(48)
<223> OTHER INFORMATION: Xaa = Asn, Ser or Thr
<220> FEATURE:
<221> NAME/KEY: misc_feature
<222> LOCATION: (49)..(49)
<223> OTHER INFORMATION: Xaa = Thr or Ser
<220> FEATURE:
<221> NAME/KEY: misc_feature
<222> LOCATION: (51)..(51)
<223> OTHER INFORMATION: Xaa = Glu, Gln, Arg or Lys
<220> FEATURE:
<221> NAME/KEY: misc_feature
<222> LOCATION: (54)..(54)
<223> OTHER INFORMATION: Xaa = Thr, Ser or Cys
```

-continued

```
<220> FEATURE:
<221> NAME/KEY: misc_feature
<222> LOCATION: (56)..(56)
<223> OTHER INFORMATION: Xaa = Ile or Val
<220> FEATURE:
<221> NAME/KEY: misc_feature
<222> LOCATION: (59)..(59)
<223> OTHER INFORMATION: Xaa = Asn, Lys or Ser
<220> FEATURE:
<221> NAME/KEY: misc_feature
<222> LOCATION: (60)..(60)
<223> OTHER INFORMATION: Xaa = Glu or Asp
<220> FEATURE:
<221> NAME/KEY: misc_feature
<222> LOCATION: (62)..(62)
<223> OTHER INFORMATION: Xaa = Ser, Thr, Ile or Asn
<220> FEATURE:
<221> NAME/KEY: misc_feature
<222> LOCATION: (68)..(68)
<223> OTHER INFORMATION: Xaa = Glu or Asp
<220> FEATURE:
<221> NAME/KEY: misc_feature
<222> LOCATION: (69)..(69)
<223> OTHER INFORMATION: Xaa = Ile or Val
<220> FEATURE:
<221> NAME/KEY: misc_feature
<222> LOCATION: (70)..(70)
<223> OTHER INFORMATION: Xaa = Ser or Gly
<220> FEATURE:
<221> NAME/KEY: misc_feature
<222> LOCATION: (72)..(72)
<223> OTHER INFORMATION: Xaa = Thr, Asn, Ala or Ser
<220> FEATURE:
<221> NAME/KEY: misc_feature
<222> LOCATION: (78)..(78)
<223> OTHER INFORMATION: Xaa = Lys or Arg
<220> FEATURE:
<221> NAME/KEY: misc_feature
<222> LOCATION: (79)..(79)
<223> OTHER INFORMATION: Xaa = Lys or Arg

<400> SEQUENCE: 7

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Glu Ile
                20                  25                  30

Leu Ile Tyr Glu Met Leu Phe Gly Xaa Thr Pro Phe Lys Xaa Xaa Xaa
            35                  40                  45

Xaa Asn Xaa Thr Phe Xaa Asn Xaa Leu Lys Xaa Xaa Val Xaa Phe Pro
        50                  55                  60

Asn Asn Asn Xaa Xaa Xaa Arg Xaa Cys Lys Asp Leu Ile Xaa Xaa Leu
65                  70                  75                  80

<210> SEQ ID NO 8
<211> LENGTH: 2682
<212> TYPE: DNA
<213> ORGANISM: Saccharomyces cerevisiae
<220> FEATURE:
<221> NAME/KEY: CDS
<222> LOCATION: (1)..(2682)

<400> SEQUENCE: 8 atg gct gga cac cat cac gaa cat gaa caa gag cgc gac cac gag caa      48
Met Ala Gly His His His Glu His Glu Gln Glu Arg Asp His Glu Gln
1               5                   10                  15 gaa cac gaa cac gat tcc ctt caa cgg cct act act gga tca gaa agg      96
Glu His Glu His Asp Ser Leu Gln Arg Pro Thr Thr Gly Ser Glu Arg
                20                  25                  30 act aga agt ata tcc ttt tcg aag ttg ctt acg cgg tca tgg aaa agg     144
Thr Arg Ser Ile Ser Phe Ser Lys Leu Leu Thr Arg Ser Trp Lys Arg
```

-continued

```
              35                  40                  45
aat gcg agt tca tcg aac aac atg agt gtg tct agc gtg aat ctg tat      192
Asn Ala Ser Ser Ser Asn Asn Met Ser Val Ser Ser Val Asn Leu Tyr
     50                  55                  60 tcg gat cca gag aac tcg aga gaa tca gat cac aat aat agt ggc tca      240
Ser Asp Pro Glu Asn Ser Arg Glu Ser Asp His Asn Asn Ser Gly Ser
 65                  70                  75                  80 gag ggc cag tct tca cga ttt tct aaa ttg aaa agt atg ttc caa tcc      288
Glu Gly Gln Ser Ser Arg Phe Ser Lys Leu Lys Ser Met Phe Gln Ser
                 85                  90                  95 ggc aat agc agc aaa aat gcc agt gcc cat aac agc agc caa agc agt      336
Gly Asn Ser Ser Lys Asn Ala Ser Ala His Asn Ser Ser Gln Ser Ser
             100                 105                 110 ctt gaa ggt gat tcg gcg tca tct tca tct aag tta aga tac gtt aaa      384
Leu Glu Gly Asp Ser Ala Ser Ser Ser Ser Lys Leu Arg Tyr Val Lys
         115                 120                 125 cca atg act tct gtt gcc aat gct tct ccg gca tct cca cca ctt tct      432
Pro Met Thr Ser Val Ala Asn Ala Ser Pro Ala Ser Pro Pro Leu Ser
     130                 135                 140 ccc acg atc ccg gaa acg gat gtt ctt caa aca cca aag atg gta cat      480
Pro Thr Ile Pro Glu Thr Asp Val Leu Gln Thr Pro Lys Met Val His
145                 150                 155                 160 ata gat caa cat gaa cat gag cgt gaa cac tcg aat tgc ggg tct cca      528
Ile Asp Gln His Glu His Glu Arg Glu His Ser Asn Cys Gly Ser Pro
                 165                 170                 175 ata atg ctt tca tca tcc tct ttc agt cct act gtt gcc agg act ggg      576
Ile Met Leu Ser Ser Ser Ser Phe Ser Pro Thr Val Ala Arg Thr Gly
             180                 185                 190 acg ggt agg aga aga tca ccg tct act ccg ata atg ccc agt cag aac      624
Thr Gly Arg Arg Arg Ser Pro Ser Thr Pro Ile Met Pro Ser Gln Asn
         195                 200                 205 tcg aat aac tct agt agc acc tct gct atc aga cca aat aat tat cgt      672
Ser Asn Asn Ser Ser Ser Thr Ser Ala Ile Arg Pro Asn Asn Tyr Arg
     210                 215                 220 cac cat tca gga tct cag ggg ttt tct tcc aac aat cca ttc aga gaa      720
His His Ser Gly Ser Gln Gly Phe Ser Ser Asn Asn Pro Phe Arg Glu
225                 230                 235                 240 agg gca ggt acg gta cgc agt agt aac cca tat ttt gca tac caa ggt      768
Arg Ala Gly Thr Val Arg Ser Ser Asn Pro Tyr Phe Ala Tyr Gln Gly
                 245                 250                 255 cta cca act cat gcc atg tct tct cat gac ctc gat gaa gga ttc caa      816
Leu Pro Thr His Ala Met Ser Ser His Asp Leu Asp Glu Gly Phe Gln
             260                 265                 270 cca tat gca aat ggc agc ggc att cac ttt ttg tcc acc ccc acc tcg      864
Pro Tyr Ala Asn Gly Ser Gly Ile His Phe Leu Ser Thr Pro Thr Ser
         275                 280                 285 aag aca aat tct ttg aca aac acc aaa aat tta agt aat tta tca cta      912
Lys Thr Asn Ser Leu Thr Asn Thr Lys Asn Leu Ser Asn Leu Ser Leu
     290                 295                 300 aac gag att aag gaa aat gaa gaa gtg caa gaa ttc aat aac gag gat      960
Asn Glu Ile Lys Glu Asn Glu Glu Val Gln Glu Phe Asn Asn Glu Asp
305                 310                 315                 320 ttc ttc ttt cac gat att ccg aaa gat tta tcg ctc aaa gat acg ctg     1008
Phe Phe Phe His Asp Ile Pro Lys Asp Leu Ser Leu Lys Asp Thr Leu
                 325                 330                 335 aat ggc tca ccc agt aga ggt agt tcc aag agc ccc acg att act caa     1056
Asn Gly Ser Pro Ser Arg Gly Ser Ser Lys Ser Pro Thr Ile Thr Gln
             340                 345                 350 acg ttc cct tca atc att gtc gga ttt gac aat gag tac gag gaa gat     1104
```

```
Thr Phe Pro Ser Ile Ile Val Gly Phe Asp Asn Glu Tyr Glu Glu Asp
            355                 360                 365 aac aac aat gat aaa cat gat gaa aag gaa gaa caa caa acg aca acc      1152
Asn Asn Asn Asp Lys His Asp Glu Lys Glu Glu Gln Gln Thr Thr Thr
370                 375                 380 aac aat aaa acg aga aat ctt tca cct acc aaa caa aat ggt aaa gct      1200
Asn Asn Lys Thr Arg Asn Leu Ser Pro Thr Lys Gln Asn Gly Lys Ala
385                 390                 395                 400 acc cat cca agg ata aaa ata cct tta aga aga gca gct tca gaa cca      1248
Thr His Pro Arg Ile Lys Ile Pro Leu Arg Arg Ala Ala Ser Glu Pro
                405                 410                 415 aac ggg ttg caa ctc gca tct gcc aca tcg ccg aca tct tct tca gca      1296
Asn Gly Leu Gln Leu Ala Ser Ala Thr Ser Pro Thr Ser Ser Ser Ala
            420                 425                 430 agg aaa aca tca ggg tcc agt aat ata aac gac aaa atc cca ggc caa      1344
Arg Lys Thr Ser Gly Ser Ser Asn Ile Asn Asp Lys Ile Pro Gly Gln
            435                 440                 445 tca gtg cct cct cca aac tca ttt ttc cct caa gaa ccc cct cca aag      1392
Ser Val Pro Pro Pro Asn Ser Phe Phe Pro Gln Glu Pro Pro Pro Lys
450                 455                 460 att tct gat ttt cca gaa cct agg agg tcc cga cgt ttg aga act aaa      1440
Ile Ser Asp Phe Pro Glu Pro Arg Arg Ser Arg Arg Leu Arg Thr Lys
465                 470                 475                 480 tct ttc agc aat aaa ttt caa gat atc atg gtg gga cca cag tct ttt      1488
Ser Phe Ser Asn Lys Phe Gln Asp Ile Met Val Gly Pro Gln Ser Phe
                485                 490                 495 gag aaa ata aga ttg ctg ggc caa ggt gat gta ggt aaa gtt ttc tta      1536
Glu Lys Ile Arg Leu Leu Gly Gln Gly Asp Val Gly Lys Val Phe Leu
            500                 505                 510 gta aga gag aaa aag acg aat aga gtg tat gct ttg aaa gtc ttg agt      1584
Val Arg Glu Lys Lys Thr Asn Arg Val Tyr Ala Leu Lys Val Leu Ser
            515                 520                 525 aaa gac gaa atg ata aaa aga aat aaa atc aaa cgt gtt ctg aca gaa      1632
Lys Asp Glu Met Ile Lys Arg Asn Lys Ile Lys Arg Val Leu Thr Glu
530                 535                 540 caa gag att ctt gcc acc agc aat cat ccc ttc atc gtc aca cta tac      1680
Gln Glu Ile Leu Ala Thr Ser Asn His Pro Phe Ile Val Thr Leu Tyr
545                 550                 555                 560 cat tcg ttc caa tct gaa gac tat ttg tat ctc tgt atg gaa tac tgt      1728
His Ser Phe Gln Ser Glu Asp Tyr Leu Tyr Leu Cys Met Glu Tyr Cys
                565                 570                 575 atg ggc ggg gag ttt ttc aga gct tta caa aca agg aaa acc aaa tgt      1776
Met Gly Gly Glu Phe Phe Arg Ala Leu Gln Thr Arg Lys Thr Lys Cys
            580                 585                 590 ata tgt gaa gac gat gcc agg ttt tat gcc agt gaa gtg aca gca gca      1824
Ile Cys Glu Asp Asp Ala Arg Phe Tyr Ala Ser Glu Val Thr Ala Ala
            595                 600                 605 cta gaa tat tta cat ctg ttg ggt ttt atc tat aga gat tta aaa cca      1872
Leu Glu Tyr Leu His Leu Leu Gly Phe Ile Tyr Arg Asp Leu Lys Pro
610                 615                 620 gag aat att ttg ctg cat caa tca ggc cat atc atg ctt tct gac ttc      1920
Glu Asn Ile Leu Leu His Gln Ser Gly His Ile Met Leu Ser Asp Phe
625                 630                 635                 640 gac ttg tct att caa gct aaa gat tcc aag gtt cct gtt gtc aag ggt      1968
Asp Leu Ser Ile Gln Ala Lys Asp Ser Lys Val Pro Val Val Lys Gly
                645                 650                 655 tcc gct caa tca acc ctt gtt gat acc aaa ata tgc tca gat ggg ttt      2016
Ser Ala Gln Ser Thr Leu Val Asp Thr Lys Ile Cys Ser Asp Gly Phe
            660                 665                 670
```

| | | | | | | | | | | | | | | | |
|---|---|---|---|---|---|---|---|---|---|---|---|---|---|---|---|
| aga | acc | aat | tcc | ttt | gtc | gga | act | gaa | gaa | tat | att | gcc | cct | gaa | gtc | 2064
| Arg | Thr | Asn | Ser | Phe | Val | Gly | Thr | Glu | Glu | Tyr | Ile | Ala | Pro | Glu | Val
| | | 675 | | | | | 680 | | | | | 685 | | |

```
aga acc aat tcc ttt gtc gga act gaa gaa tat att gcc cct gaa gtc      2064
Arg Thr Asn Ser Phe Val Gly Thr Glu Glu Tyr Ile Ala Pro Glu Val
        675                 680                 685 ata aga ggt aat ggc cac acc gct gcg gtc gat tgg tgg acg cta gag      2112
Ile Arg Gly Asn Gly His Thr Ala Ala Val Asp Trp Trp Thr Leu Glu
690                 695                 700 att ttg atc tat gaa atg tta ttt ggt ttc act cca ttc aaa ggc gat      2160
Ile Leu Ile Tyr Glu Met Leu Phe Gly Phe Thr Pro Phe Lys Gly Asp
705                 710                 715                 720 aac aca aat gaa act ttt acg aat att ttg aaa aat gag gtc agt ttt      2208
Asn Thr Asn Glu Thr Phe Thr Asn Ile Leu Lys Asn Glu Val Ser Phe
            725                 730                 735 ccc aat aac aat gaa atc tcc aga act tgt aag gat ttg atc aaa aaa      2256
Pro Asn Asn Asn Glu Ile Ser Arg Thr Cys Lys Asp Leu Ile Lys Lys
            740                 745                 750 tta ctg aca aaa aat gaa tct aaa aga ctg ggt tgc aaa atg ggc gct      2304
Leu Leu Thr Lys Asn Glu Ser Lys Arg Leu Gly Cys Lys Met Gly Ala
            755                 760                 765 gcc gac gtg aag aaa cac ccc ttt ttc aag aaa gtc caa tgg tct ttg      2352
Ala Asp Val Lys Lys His Pro Phe Phe Lys Lys Val Gln Trp Ser Leu
770                 775                 780 ctg aga aat caa gaa ccg cct ctg ata cca gtg tta tct gag gat gga      2400
Leu Arg Asn Gln Glu Pro Pro Leu Ile Pro Val Leu Ser Glu Asp Gly
785                 790                 795                 800 tat gat ttt gct aaa tta tca tct aat aag aag aga cag act agt caa      2448
Tyr Asp Phe Ala Lys Leu Ser Ser Asn Lys Lys Arg Gln Thr Ser Gln
            805                 810                 815 gac agc cat aaa cat ctc gat gag caa gag aaa aat atg ttt gaa gaa      2496
Asp Ser His Lys His Leu Asp Glu Gln Glu Lys Asn Met Phe Glu Glu
            820                 825                 830 cga gtt gaa tac gac gat gaa gtc tct gaa gat gat cca ttc cat gac      2544
Arg Val Glu Tyr Asp Asp Glu Val Ser Glu Asp Asp Pro Phe His Asp
835                 840                 845 ttc aat tca atg agt ttg atg gaa cag gat aac aat tca atg att tat      2592
Phe Asn Ser Met Ser Leu Met Glu Gln Asp Asn Asn Ser Met Ile Tyr
850                 855                 860 ggt aat acc aat tct tat ggg aaa att gca tac act cca aac tcc aac      2640
Gly Asn Thr Asn Ser Tyr Gly Lys Ile Ala Tyr Thr Pro Asn Ser Asn
865                 870                 875                 880 aga tcg agg agt aat agt cat cga acc ttt ttt aag aga taa              2682
Arg Ser Arg Ser Asn Ser His Arg Thr Phe Phe Lys Arg
            885                 890
```

<210> SEQ ID NO 9
<211> LENGTH: 893
<212> TYPE: PRT
<213> ORGANISM: Saccharomyces cerevisiae

<400> SEQUENCE: 9

```
Met Ala Gly His His His Glu His Glu Gln Glu Arg Asp His Glu Gln
1               5                   10                  15

Glu His Glu His Asp Ser Leu Gln Arg Pro Thr Thr Gly Ser Glu Arg
            20                  25                  30

Thr Arg Ser Ile Ser Phe Ser Lys Leu Leu Thr Arg Ser Trp Lys Arg
        35                  40                  45

Asn Ala Ser Ser Ser Asn Asn Met Ser Val Ser Ser Val Asn Leu Tyr
    50                  55                  60

Ser Asp Pro Glu Asn Ser Arg Glu Ser Asp His Asn Asn Ser Gly Ser
65                  70                  75                  80
```

```
Glu Gly Gln Ser Ser Arg Phe Ser Lys Leu Lys Ser Met Phe Gln Ser
                85                  90                  95

Gly Asn Ser Ser Lys Asn Ala Ser Ala His Asn Ser Ser Gln Ser Ser
            100                 105                 110

Leu Glu Gly Asp Ser Ala Ser Ser Ser Lys Leu Arg Tyr Val Lys
        115                 120                 125

Pro Met Thr Ser Val Ala Asn Ala Ser Pro Ala Ser Pro Leu Ser
    130                 135                 140

Pro Thr Ile Pro Glu Thr Asp Val Leu Gln Thr Pro Lys Met Val His
145                 150                 155                 160

Ile Asp Gln His Glu His Glu Arg Glu His Ser Asn Cys Gly Ser Pro
                165                 170                 175

Ile Met Leu Ser Ser Ser Ser Phe Ser Pro Thr Val Ala Arg Thr Gly
                180                 185                 190

Thr Gly Arg Arg Arg Ser Pro Ser Thr Pro Ile Met Pro Ser Gln Asn
            195                 200                 205

Ser Asn Asn Ser Ser Ser Thr Ser Ala Ile Arg Pro Asn Asn Tyr Arg
210                 215                 220

His His Ser Gly Ser Gln Gly Phe Ser Ser Asn Asn Pro Phe Arg Glu
225                 230                 235                 240

Arg Ala Gly Thr Val Arg Ser Ser Asn Pro Tyr Phe Ala Tyr Gln Gly
            245                 250                 255

Leu Pro Thr His Ala Met Ser Ser His Asp Leu Asp Glu Gly Phe Gln
            260                 265                 270

Pro Tyr Ala Asn Gly Ser Gly Ile His Phe Leu Ser Thr Pro Thr Ser
        275                 280                 285

Lys Thr Asn Ser Leu Thr Asn Thr Lys Asn Leu Ser Asn Leu Ser Leu
290                 295                 300

Asn Glu Ile Lys Glu Asn Glu Glu Val Gln Glu Phe Asn Asn Glu Asp
305                 310                 315                 320

Phe Phe Phe His Asp Ile Pro Lys Asp Leu Ser Leu Lys Asp Thr Leu
                325                 330                 335

Asn Gly Ser Pro Ser Arg Gly Ser Ser Lys Ser Pro Thr Ile Thr Gln
            340                 345                 350

Thr Phe Pro Ser Ile Ile Val Gly Phe Asp Asn Glu Tyr Glu Glu Asp
            355                 360                 365

Asn Asn Asn Asp Lys His Asp Glu Lys Glu Glu Gln Gln Thr Thr Thr
        370                 375                 380

Asn Asn Lys Thr Arg Asn Leu Ser Pro Thr Lys Gln Asn Gly Lys Ala
385                 390                 395                 400

Thr His Pro Arg Ile Lys Ile Pro Leu Arg Arg Ala Ala Ser Glu Pro
                405                 410                 415

Asn Gly Leu Gln Leu Ala Ser Ala Thr Ser Pro Thr Ser Ser Ser Ala
            420                 425                 430

Arg Lys Thr Ser Gly Ser Ser Asn Ile Asn Asp Lys Ile Pro Gly Gln
            435                 440                 445

Ser Val Pro Pro Asn Ser Phe Pro Gln Glu Pro Pro Lys
450                 455                 460

Ile Ser Asp Phe Pro Glu Pro Arg Arg Ser Arg Arg Leu Arg Thr Lys
465                 470                 475                 480

Ser Phe Ser Asn Lys Phe Gln Asp Ile Met Val Gly Pro Gln Ser Phe
                485                 490                 495

Glu Lys Ile Arg Leu Leu Gly Gln Gly Asp Val Gly Lys Val Phe Leu
```

-continued

```
                500                 505                 510
Val Arg Glu Lys Lys Thr Asn Arg Val Tyr Ala Leu Lys Val Leu Ser
            515                 520                 525

Lys Asp Glu Met Ile Lys Arg Asn Lys Ile Lys Arg Val Leu Thr Glu
530                 535                 540

Gln Glu Ile Leu Ala Thr Ser Asn His Pro Phe Ile Val Thr Leu Tyr
545                 550                 555                 560

His Ser Phe Gln Ser Glu Asp Tyr Leu Tyr Leu Cys Met Glu Tyr Cys
                565                 570                 575

Met Gly Gly Glu Phe Phe Arg Ala Leu Gln Thr Arg Lys Thr Lys Cys
            580                 585                 590

Ile Cys Glu Asp Asp Ala Arg Phe Tyr Ala Ser Glu Val Thr Ala Ala
        595                 600                 605

Leu Glu Tyr Leu His Leu Leu Gly Phe Ile Tyr Arg Asp Leu Lys Pro
    610                 615                 620

Glu Asn Ile Leu Leu His Gln Ser Gly His Ile Met Leu Ser Asp Phe
625                 630                 635                 640

Asp Leu Ser Ile Gln Ala Lys Asp Ser Lys Val Pro Val Val Lys Gly
                645                 650                 655

Ser Ala Gln Ser Thr Leu Val Asp Thr Lys Ile Cys Ser Asp Gly Phe
            660                 665                 670

Arg Thr Asn Ser Phe Val Gly Thr Glu Glu Tyr Ile Ala Pro Glu Val
        675                 680                 685

Ile Arg Gly Asn Gly His Thr Ala Ala Val Asp Trp Trp Thr Leu Glu
    690                 695                 700

Ile Leu Ile Tyr Glu Met Leu Phe Gly Phe Thr Pro Phe Lys Gly Asp
705                 710                 715                 720

Asn Thr Asn Glu Thr Phe Thr Asn Ile Leu Lys Asn Glu Val Ser Phe
                725                 730                 735

Pro Asn Asn Asn Glu Ile Ser Arg Thr Cys Lys Asp Leu Ile Lys Lys
            740                 745                 750

Leu Leu Thr Lys Asn Glu Ser Lys Arg Leu Gly Cys Lys Met Gly Ala
        755                 760                 765

Ala Asp Val Lys Lys His Pro Phe Phe Lys Lys Val Gln Trp Ser Leu
    770                 775                 780

Leu Arg Asn Gln Glu Pro Pro Leu Ile Pro Val Leu Ser Glu Asp Gly
785                 790                 795                 800

Tyr Asp Phe Ala Lys Leu Ser Ser Asn Lys Lys Arg Gln Thr Ser Gln
                805                 810                 815

Asp Ser His Lys His Leu Asp Glu Gln Glu Lys Asn Met Phe Glu Glu
            820                 825                 830

Arg Val Glu Tyr Asp Asp Glu Val Ser Glu Asp Pro Phe His Asp
        835                 840                 845

Phe Asn Ser Met Ser Leu Met Glu Gln Asp Asn Asn Ser Met Ile Tyr
    850                 855                 860

Gly Asn Thr Asn Ser Tyr Gly Lys Ile Ala Tyr Thr Pro Asn Ser Asn
865                 870                 875                 880

Arg Ser Arg Ser Asn Ser His Arg Thr Phe Phe Lys Arg
                885                 890

<210> SEQ ID NO 10
<211> LENGTH: 66
<212> TYPE: PRT
<213> ORGANISM: Saccharomyces cerevisiae
```

```
<400> SEQUENCE: 10

Glu Asp Tyr Glu Leu Arg Leu Val Thr Arg His Asn Thr Gly Arg Phe
1               5                   10                  15

Ala Ser Lys Glu His Ser Glu Asn His Val Pro Gln Asp Cys Val Glu
            20                  25                  30

Ala Ser Leu Asn Pro Glu Ala Ile Arg Glu Leu Thr Gln Lys Trp Lys
        35                  40                  45

Glu Leu Leu Ser Gln Gln Ala Lys Glu Glu Ser Ser Asp Ser Glu Ser
    50                  55                  60

Glu Thr
65

<210> SEQ ID NO 11
<211> LENGTH: 66
<212> TYPE: PRT
<213> ORGANISM: Saccharomyces cerevisiae

<400> SEQUENCE: 11

Glu Asp Tyr Glu Leu Arg Leu Val Thr Arg His Asn Thr Gly Arg Phe
1               5                   10                  15

Ala Ser Lys Glu His Ser Glu Asn His Val Pro Gln Asp Leu Val Glu
            20                  25                  30

Ala Ser Leu Asn Pro Glu Ala Ile Arg Glu Leu Thr Gln Lys Trp Lys
        35                  40                  45

Glu Leu Leu Ser Gln Gln Ala Lys Glu Glu Ser Ser Asp Ser Glu Ser
    50                  55                  60

Glu Thr
65

<210> SEQ ID NO 12
<211> LENGTH: 66
<212> TYPE: PRT
<213> ORGANISM: Saccharomyces kudriavzevii

<400> SEQUENCE: 12

Glu Asp Tyr Glu Leu Arg Leu Val Thr Ser His Asn Thr Cys Arg Phe
1               5                   10                  15

Ala Ser Lys Glu His Ser Glu Asn His Val Pro Gln Asp Leu Val Glu
            20                  25                  30

Ala Ser Leu Asn Pro Glu Ala Ile Arg Glu Leu Thr Gln Lys Trp Lys
        35                  40                  45

Glu Leu Leu Ser Gln Gln Thr Gln Glu Glu Ser Ser Asp Ser Glu Asp
    50                  55                  60

Gly Thr
65

<210> SEQ ID NO 13
<211> LENGTH: 66
<212> TYPE: PRT
<213> ORGANISM: Saccharomyces eubayanus

<400> SEQUENCE: 13

Glu Asp Tyr Glu Leu Arg Leu Val Thr Arg His Asn Thr Gly Arg Phe
1               5                   10                  15

Ala Ser Lys Glu His Ser Glu Asn His Val Pro Gln Asp Leu Val Glu
            20                  25                  30

Ala Gly Leu Asp Pro Glu Ala Ile Arg Glu Leu Thr Gln Lys Trp Arg
```

```
                35                  40                  45

Glu Leu Leu Asn Gln Gln Thr Gln Glu Glu Ser Ser Gly Ser Glu Asp
     50                  55                  60

Glu Ala
65

<210> SEQ ID NO 14
<211> LENGTH: 62
<212> TYPE: PRT
<213> ORGANISM: Candida glabrata

<400> SEQUENCE: 14

Arg Asp Tyr Glu Leu Arg Leu Ile Thr Glu Asn Asn Ile Gly Arg Phe
1               5                   10                  15

Ala Ser Lys Glu His Ser Gln Asn His Val Pro Lys Asp Val Val Asp
                20                  25                  30

Ala Ser Leu Asp Pro Glu Arg Ile Arg Glu Leu Ser Gln Lys Trp Ser
            35                  40                  45

Glu Leu Leu Gln Gln Glu Lys Glu Ser Ser Asp Glu Glu
     50                  55                  60

<210> SEQ ID NO 15
<211> LENGTH: 67
<212> TYPE: PRT
<213> ORGANISM: Kazachstania naganishii

<400> SEQUENCE: 15

Gln Asp Tyr Glu Leu Arg Leu Val Lys Glu Asn Asn Thr Ala Arg Phe
1               5                   10                  15

Ala Ser Lys Glu His Ser Glu Asn His Val Pro Lys Asp Ile Val Asp
                20                  25                  30

Ala Ser Leu Asp Pro Asn Ala Ile Arg Asp Leu Ala Gln Lys Trp Lys
            35                  40                  45

Glu Leu Leu Ser Gln Gln Gln Ala Glu Asp Ser Ser Ser Gly Ser Glu
     50                  55                  60

Glu Glu Ala
65

<210> SEQ ID NO 16
<211> LENGTH: 61
<212> TYPE: PRT
<213> ORGANISM: Naumovozyma dairenensis

<400> SEQUENCE: 16

Lys Asp Tyr Glu Leu Arg Leu Val Lys Glu Asn Asn Val Gly Arg Phe
1               5                   10                  15

Val Ser Lys Glu His Ser Glu Asn Gln Val Pro Lys Asp Leu Ile Asp
                20                  25                  30

Ala Ala Leu Asp Pro Gln Ala Ile Lys Glu Leu Thr Glu Lys Trp Lys
            35                  40                  45

Glu Leu Leu Ser Arg Gln Glu Lys Asp Glu Glu Asn Lys
     50                  55                  60

<210> SEQ ID NO 17
<211> LENGTH: 66
<212> TYPE: PRT
<213> ORGANISM: Tetrapisispora blattae

<400> SEQUENCE: 17
```

```
Arg Asp Tyr Glu Leu Arg Leu Val Lys Arg Asn Asn Val Ala Arg Phe
  1               5                  10                  15

Ala Ser Lys Glu His Ser Glu Asn Gln Val Pro Lys Asp Val Val Asp
             20                  25                  30

Ala Ser Leu Asp Pro Asn Val Ile Lys Glu Leu Ala Ser Lys Trp Lys
             35                  40                  45

Glu Leu Leu Ser Gln Gln Glu Ala Asp Thr Asp Ser Asp Ser Asp Ser
 50                  55                  60

Ala Glu
 65

<210> SEQ ID NO 18
<211> LENGTH: 67
<212> TYPE: PRT
<213> ORGANISM: Naumovozyma castellii

<400> SEQUENCE: 18

Lys Asp Tyr Glu Leu Arg Leu Leu Thr Glu Asn Asn Thr Gly Arg Phe
  1               5                  10                  15

Ala Ser Lys Glu His Ser Glu Asn Gln Val Pro Arg Asp Leu Val Asp
             20                  25                  30

Ala Ser Leu Asn Pro Asp Ala Ile Arg Glu Leu Thr Gln Lys Trp Lys
             35                  40                  45

Asp Leu Leu Ser Arg Gln Asn Gly Ser Gly Ser Asp Thr Glu Ser Glu
 50                  55                  60

Ser Glu Ser
 65

<210> SEQ ID NO 19
<211> LENGTH: 63
<212> TYPE: PRT
<213> ORGANISM: Torulaspora delbrueckii

<400> SEQUENCE: 19

Glu Asp Tyr Glu Leu Arg Ile Val Pro Glu Asn Asn Val Ala Arg Phe
  1               5                  10                  15

Ala Thr Lys Glu His Ser Glu Asn His Val Pro Lys Asp Val Leu Glu
             20                  25                  30

Ala Ser Leu Asn Pro Glu Ala Ile Lys Glu Leu Ser Glu Lys Trp Gln
             35                  40                  45

Glu Leu Leu Arg Cys Gln Glu Leu Glu Asp Asp Ser Asp Asn Glu
 50                  55                  60

<210> SEQ ID NO 20
<211> LENGTH: 61
<212> TYPE: PRT
<213> ORGANISM: Kazachstania africana

<400> SEQUENCE: 20

Lys Asp Tyr Glu Leu Arg Leu Val Leu Glu Asn Asn Thr Ala Arg Phe
  1               5                  10                  15

Ala Ser Lys Glu His Ser Glu Asn Gln Val Pro Arg Asp Val Val Asp
             20                  25                  30

Ala Thr Thr Asp Pro Asn Ala Ile Arg Glu Leu Ile Gly Lys Trp Lys
             35                  40                  45

Glu Leu Leu Glu Gln Gln Glu Glu Asp Thr Asp Ser Asp
 50                  55                  60
```

<210> SEQ ID NO 21
<211> LENGTH: 64
<212> TYPE: PRT
<213> ORGANISM: Tetrapisispora phaffii

<400> SEQUENCE: 21

Asp Asp Tyr Glu Leu Arg Leu Leu Thr Glu Thr Asn Val Gly Arg Phe
1               5                   10                  15

Ala His Lys Glu His Ser Glu Asn Gln Val Pro Ile Asp Ile Val Glu
            20                  25                  30

Ala Ser Leu Asn Pro Asp Ala Ile Lys Glu Leu Ala Asp Lys Trp Ser
        35                  40                  45

Glu Leu Leu Lys Lys Gln Asp Asp Tyr Asp Ser Asp Ser His Asp Asn
    50                  55                  60

<210> SEQ ID NO 22
<211> LENGTH: 66
<212> TYPE: PRT
<213> ORGANISM: Vanderwaltozyma polyspora

<400> SEQUENCE: 22

Glu Asp Tyr Glu Phe Arg Leu Ile Lys Glu Asn Asn Val Gly Arg Phe
1               5                   10                  15

Ala Cys Lys Glu His Ser Glu Asn Gln Val Pro Thr Asp Ile Val Glu
            20                  25                  30

Ala Ser Leu Asn Pro Glu Ala Ile Arg Glu Leu Thr Gln Lys Trp Lys
        35                  40                  45

Glu Leu Leu Ser Lys Gln Ser Met Glu Glu Asp Ser Ser Ser Asp Ser
    50                  55                  60

Asn Glu
65

<210> SEQ ID NO 23
<211> LENGTH: 70
<212> TYPE: PRT
<213> ORGANISM: Saccharomyces cerevisiae

<400> SEQUENCE: 23

Lys Glu Pro Thr Asp Asp Ile Ala Glu Ala Leu Gly Glu Leu Ser Leu
1               5                   10                  15

Lys Lys Lys Lys Lys Lys Thr Lys Asp Ser Ser Val Asp Ala Phe Glu
            20                  25                  30

Lys Glu Leu Ala Lys Ala Gly Leu Asp Asn Val Asp Ala Glu Thr Lys
        35                  40                  45

Glu Gly Thr Pro Ser Ala Asn Ser Ser Ile Gln Gln Glu Val Gly Leu
    50                  55                  60

Pro Tyr Ser Glu Leu Leu
65                  70

<210> SEQ ID NO 24
<211> LENGTH: 70
<212> TYPE: PRT
<213> ORGANISM: Saccharomyces cerevisiae

<400> SEQUENCE: 24

Lys Glu Pro Thr Asp Asp Ile Ala Glu Ala Phe Gly Glu Leu Ser Leu
1               5                   10                  15

Lys Lys Lys Lys Lys Lys Thr Lys Asp Ser Ser Val Asp Ala Phe Glu
            20                  25                  30

```
Lys Glu Leu Ala Lys Ala Gly Leu Asp Asn Val Asp Ala Glu Ser Lys
            35                  40                  45

Glu Gly Thr Pro Ser Ala Asn Ser Ser Ile Gln Gln Glu Val Gly Leu
        50                  55                  60

Pro Tyr Ser Glu Leu Leu
65                  70

<210> SEQ ID NO 25
<211> LENGTH: 70
<212> TYPE: PRT
<213> ORGANISM: Saccharomyces eubayanus

<400> SEQUENCE: 25

Thr Glu Pro Thr Asp Asp Ile Ala Glu Ala Leu Gly Glu Leu Ser Leu
1               5                   10                  15

Lys Lys Lys Lys Lys Lys Thr Lys Asp Ser Ser Val Asp Ala Phe Glu
                20                  25                  30

Lys Glu Leu Ala Lys Ala Gly Leu Asp Asn Val Asp Ala Glu Ser Lys
            35                  40                  45

Glu Ala Thr Pro Ala Ala Ser Ala Ser Ile Gln Gln Glu Val Gly Leu
        50                  55                  60

Pro Tyr Pro Glu Leu Leu
65                  70

<210> SEQ ID NO 26
<211> LENGTH: 70
<212> TYPE: PRT
<213> ORGANISM: Saccharomyces arboricola

<400> SEQUENCE: 26

Lys Gly Pro Thr Asp Asp Ile Ala Glu Ala Leu Gly Glu Leu Ser Leu
1               5                   10                  15

Lys Lys Lys Lys Lys Lys Thr Lys Asp Ser Ser Val Asp Ala Phe Glu
                20                  25                  30

Lys Glu Leu Ala Lys Ala Gly Leu Asp Ser Val Glu Gly Glu Ser Lys
            35                  40                  45

Glu Ala Thr Pro Val Ala Ser Ser Ser Ile Gln Gln Glu Val Gly Leu
        50                  55                  60

Pro Tyr Pro Glu Leu Leu
65                  70

<210> SEQ ID NO 27
<211> LENGTH: 67
<212> TYPE: PRT
<213> ORGANISM: Kazachstania africana

<400> SEQUENCE: 27

Asp Asn Thr Thr Asp Asp Ile Thr Glu Ala Leu Gly Glu Leu Ser Leu
1               5                   10                  15

Lys Lys Lys Lys Lys Lys Thr Lys Asp Val Ala Leu Asp Asp Phe Glu
                20                  25                  30

Lys Glu Leu Ala Lys Ala Gly Val Thr Ser Glu Ser Lys Glu Thr Thr
            35                  40                  45

Pro Gln Asn Ile Ser Val Val Gln Gln Glu Ala Gly Leu Pro Tyr Asp
        50                  55                  60

Lys Leu Leu
65
```

<210> SEQ ID NO 28
<211> LENGTH: 67
<212> TYPE: PRT
<213> ORGANISM: Kazachstania naganishii

<400> SEQUENCE: 28

Asp Gly Glu Leu Asp Asp Val Ser Glu Ala Leu Gly Glu Leu Thr Leu
1               5                   10                  15

Lys Lys Lys Lys Lys Lys Ser Lys Asp Ser Thr Leu Asp Asp Phe Glu
            20                  25                  30

Lys Glu Leu Ala Arg Ala Gly Ile Asn Glu Glu Ser Ser Lys Asp Ser
        35                  40                  45

Thr Pro Thr Gly Glu Ile Gly Asn Asp Glu Val Gly Leu Pro Tyr Ala
    50                  55                  60

Asp Leu Leu
65

<210> SEQ ID NO 29
<211> LENGTH: 69
<212> TYPE: PRT
<213> ORGANISM: Naumovozyma castellii

<400> SEQUENCE: 29

Asn Asn Ser Val Asp Glu Leu Ser Asp Val Leu Gly Asp Leu Thr Ile
1               5                   10                  15

Lys Lys Lys Lys Lys Ala Ala His Val Asp Val Asp Ala Phe Glu
            20                  25                  30

Lys Glu Leu Ala Lys Ala Gly Val Ser Thr Glu Ser Lys Glu Ala Thr
        35                  40                  45

Pro Ser Gly Asp Asn Glu Ser Ser Ile Gln Asn Ser Ile Gly Leu Pro
    50                  55                  60

Tyr Pro Glu Leu Leu
65

<210> SEQ ID NO 30
<211> LENGTH: 70
<212> TYPE: PRT
<213> ORGANISM: Torulaspora delbrueckii

<400> SEQUENCE: 30

Ser Asp Ser Val Asp Asp Ile Ser Glu Ala Leu Gly Glu Leu Lys Leu
1               5                   10                  15

Lys Lys Lys Lys Lys Ala Lys Asp Thr Asp Leu Asp Asp Phe Glu
            20                  25                  30

Gln Gln Leu Ala Lys Ala Gly Val Asn Val Asp Glu Ala Asn Asn Lys
        35                  40                  45

Glu Ala Thr Pro Thr Val Asp Ser Ala Leu Gln Gln Glu Val Gly Leu
    50                  55                  60

Ala Tyr Pro Glu Leu Leu
65                  70

<210> SEQ ID NO 31
<211> LENGTH: 72
<212> TYPE: PRT
<213> ORGANISM: Naumovozyma dairenensis

<400> SEQUENCE: 31

Asn Asn Thr Ser Val Asp Asp Leu Ser Asp Val Leu Gly Asp Leu Thr
1               5                   10                  15

```
Leu Lys Lys Lys Lys Lys Lys Ser Lys Glu Ala Thr Thr Asp Asp Phe
            20                  25                  30

Glu Lys Glu Leu Ala Lys Ala Gly Val Ser Thr Ser Lys Asp Gly Thr
        35                  40                  45

Pro Leu Ser Glu Gly Asn Ser Glu Ser Glu Thr Leu Gln Lys Glu Val
    50                  55                  60

Gly Leu Pro Tyr Pro Gln Leu Leu
65                  70

<210> SEQ ID NO 32
<211> LENGTH: 69
<212> TYPE: PRT
<213> ORGANISM: Zygosaccharomyces bailii

<400> SEQUENCE: 32

Ser Gly Ser Val Asp Glu Ile Ser Glu Ala Leu Gly Glu Leu Lys Leu
1               5                   10                  15

Lys Lys Lys Lys Lys Ser Lys Glu Thr Glu Val Asp Asp Phe Glu Gln
            20                  25                  30

Gln Leu Ala Lys Ala Gly Val Lys Val Ala Gly Gly Asn Ser Lys Glu
        35                  40                  45

Ser Thr Pro Val Ala Glu Ser Ser Ile Gln Gln Asp Val Gly Leu Thr
    50                  55                  60

Tyr Gln Asp Leu Leu
65

<210> SEQ ID NO 33
<211> LENGTH: 69
<212> TYPE: PRT
<213> ORGANISM: Tetrapisispora blattae

<400> SEQUENCE: 33

Asn Gly Glu Ile Asp Glu Ala Ser Glu Ala Leu Gly Glu Leu Ser Leu
1               5                   10                  15

Lys Lys Lys Lys Lys Lys Thr Lys Glu Ala Asn Leu Asp Glu Phe
            20                  25                  30

Glu Lys Glu Leu Ala Lys Ala Gly Val Val Val Asp Gly Asn Lys Glu
        35                  40                  45

Glu Thr Pro Ser Asn Glu Ser Thr Leu Gln Gly Asp Ile Gly Leu Pro
    50                  55                  60

Tyr Gln Asp Leu Leu
65

<210> SEQ ID NO 34
<211> LENGTH: 69
<212> TYPE: PRT
<213> ORGANISM: Zygosaccharomyces rouxii

<400> SEQUENCE: 34

Ser Glu Ser Val Asp Glu Ile Ser Glu Ala Leu Gly Glu Leu Lys Leu
1               5                   10                  15

Lys Lys Lys Lys Lys Ser Lys Glu Ala Glu Val Asp Asp Phe Glu Lys
            20                  25                  30

Gln Leu Ala Ser Ala Gly Val Asn Val Asp Gly Gly Asn Ser Gln Glu
        35                  40                  45

Ser Thr Pro Ala Leu Glu Ser Ser Leu Gln Gln Asp Val Gly Leu Ser
    50                  55                  60

Tyr Pro Gly Leu Leu
65
```

<210> SEQ ID NO 35
<211> LENGTH: 67
<212> TYPE: PRT
<213> ORGANISM: Tetrapisispora phaffii

<400> SEQUENCE: 35

Asp Val Asp Asp Ile Thr Glu Ala Leu Gly Asp Leu Lys Leu Lys Lys
1               5                   10                  15

Lys Lys Lys Lys Ala Pro Val Ala Asp Val Asp Glu Phe Glu Gln Glu
            20                  25                  30

Leu Ala Lys Ala Gly Val Val Asp Glu Thr Ser Asn Glu Ala Thr
        35                  40                  45

Pro Gly His Glu Ser Ser Leu Gln Gln Asp Val Gly Leu Pro Tyr Asp
    50                  55                  60

Lys Leu Leu
65

<210> SEQ ID NO 36
<211> LENGTH: 80
<212> TYPE: PRT
<213> ORGANISM: Saccharomyces cerevisiae

<400> SEQUENCE: 36

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Glu Ile
            20                  25                  30

Leu Ile Tyr Glu Met Leu Phe Gly Phe Thr Pro Phe Lys Gly Asp Asn
        35                  40                  45

Thr Asn Glu Thr Phe Thr Asn Ile Leu Lys Asn Glu Val Ser Phe Pro
    50                  55                  60

Asn Asn Asn Glu Ile Ser Arg Thr Cys Lys Asp Leu Ile Lys Lys Leu
65                  70                  75                  80

<210> SEQ ID NO 37
<211> LENGTH: 80
<212> TYPE: PRT
<213> ORGANISM: Saccharomyces cerevisiae

<400> SEQUENCE: 37

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Ile Tyr Glu Met Leu Phe Gly Phe Thr Pro Phe Lys Gly Asp Asn
        35                  40                  45

Thr Asn Glu Thr Phe Thr Asn Ile Leu Lys Asn Glu Val Ser Phe Pro
    50                  55                  60

Asn Asn Asn Glu Ile Ser Arg Thr Cys Lys Asp Leu Ile Lys Lys Leu
65                  70                  75                  80

<210> SEQ ID NO 38
<211> LENGTH: 80
<212> TYPE: PRT
<213> ORGANISM: Candida glabrata

<400> SEQUENCE: 38

```
Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Ile Tyr Glu Met Leu Phe Gly Phe Thr Pro Phe Lys Gly Glu Asn
        35                  40                  45

Thr Asn Glu Thr Phe Ser Asn Ile Leu Lys Lys Asp Val Thr Phe Pro
    50                  55                  60

Asn Asn Asn Glu Val Ser Arg Asn Cys Lys Asp Leu Ile Lys Lys Leu
65                  70                  75                  80

<210> SEQ ID NO 39
<211> LENGTH: 80
<212> TYPE: PRT
<213> ORGANISM: Torulaspora delbrueckii

<400> SEQUENCE: 39

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Thr Tyr Glu Met Leu Phe Gly Phe Thr Pro Phe Lys Gly Asp Asn
        35                  40                  45

Thr Asn Glu Thr Phe Cys Asn Ile Leu Lys Ser Glu Val Thr Phe Pro
    50                  55                  60

Asn Asn Asn Glu Ile Ser Arg Ala Cys Lys Asp Leu Ile Lys Lys Leu
65                  70                  75                  80

<210> SEQ ID NO 40
<211> LENGTH: 80
<212> TYPE: PRT
<213> ORGANISM: Naumovozyma castellii

<400> SEQUENCE: 40

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Ile Tyr Glu Met Leu Phe Gly Phe Thr Pro Phe Lys Gly Ser Ser
        35                  40                  45

Ser Asn Glu Thr Phe Ser Asn Ile Leu Lys Asn Asp Val Ser Phe Pro
    50                  55                  60

Asn Asn Asn Asp Ile Ser Arg Asn Cys Lys Asp Leu Ile Lys Lys Leu
65                  70                  75                  80

<210> SEQ ID NO 41
<211> LENGTH: 80
<212> TYPE: PRT
<213> ORGANISM: Lachancea fermentati

<400> SEQUENCE: 41

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Ile Tyr Glu Met Leu Phe Gly Phe Thr Pro Phe Lys Gly Asp Asn
        35                  40                  45

Thr Asn Gln Thr Phe Ser Asn Ile Leu Lys Asn Asp Val Ile Phe Pro
```

```
                 50                  55                  60

Asn Asn Asn Glu Ile Ser Arg Thr Cys Lys Asp Leu Ile Lys Arg Leu
 65                  70                  75                  80

<210> SEQ ID NO 42
<211> LENGTH: 80
<212> TYPE: PRT
<213> ORGANISM: Lachancea lanzarotensis

<400> SEQUENCE: 42

Thr Asn Ser Phe Val Gly Thr Glu Glu Tyr Leu Ala Pro Glu Val Ile
 1               5                  10                  15

Arg Gly Asn Gly His Thr Ala Ala Val Asp Trp Trp Thr Leu Gly Ile
                20                  25                  30

Leu Ile Tyr Glu Met Leu Phe Gly Phe Thr Pro Phe Lys Gly Asp Asn
             35                  40                  45

Thr Asn Arg Thr Phe Ser Asn Val Leu Lys Asn Asp Val Thr Phe Pro
         50                  55                  60

Asn Asn Asn Glu Ile Ser Arg Ser Cys Lys Asp Leu Ile Arg Arg Leu
 65                  70                  75                  80

<210> SEQ ID NO 43
<211> LENGTH: 80
<212> TYPE: PRT
<213> ORGANISM: Lachancea quebecensis

<400> SEQUENCE: 43

Thr Asn Ser Phe Val Gly Thr Glu Glu Tyr Ile Ala Pro Glu Val Ile
 1               5                  10                  15

Arg Gly Asn Gly His Thr Ala Ala Val Asp Trp Trp Thr Leu Gly Ile
                20                  25                  30

Leu Ile Tyr Glu Met Leu Phe Gly Phe Thr Pro Phe Lys Ala Asp Thr
             35                  40                  45

Thr Asn Lys Thr Phe Ser Asn Val Leu Lys Asn Glu Val Thr Phe Pro
         50                  55                  60

Asn Asn Asn Glu Ile Ser Arg Asn Cys Lys Asp Leu Ile Lys Lys Leu
 65                  70                  75                  80

<210> SEQ ID NO 44
<211> LENGTH: 80
<212> TYPE: PRT
<213> ORGANISM: Lachancea dasiensis

<400> SEQUENCE: 44

Thr Asn Ser Phe Val Gly Thr Glu Glu Tyr Ile Ala Pro Glu Val Ile
 1               5                  10                  15

Arg Gly Asn Gly His Thr Ala Ala Val Asp Trp Trp Thr Leu Gly Ile
                20                  25                  30

Leu Ile Tyr Glu Met Leu Phe Gly Phe Thr Pro Phe Lys Gly Asp Asn
             35                  40                  45

Thr Asn Lys Thr Phe Ser Asn Val Leu Lys Asn Asp Val Asn Phe Pro
         50                  55                  60

Asn Asn Asn Glu Val Ser Arg Ser Cys Lys Asp Leu Ile Arg Lys Leu
 65                  70                  75                  80

<210> SEQ ID NO 45
<211> LENGTH: 80
<212> TYPE: PRT
<213> ORGANISM: Lachancea thermotolerans
```

<400> SEQUENCE: 45

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Ile Tyr Glu Met Leu Phe Gly Phe Thr Pro Phe Lys Ala Asp Thr
        35                  40                  45

Thr Asn Lys Thr Phe Ser Asn Val Leu Lys Asn Glu Val Thr Phe Pro
    50                  55                  60

Asn Asn Asn Glu Val Ser Arg Asn Cys Lys Asp Leu Ile Lys Lys Leu
65                  70                  75                  80

<210> SEQ ID NO 46
<211> LENGTH: 80
<212> TYPE: PRT
<213> ORGANISM: Lachancea nothofagi

<400> SEQUENCE: 46

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Ile Tyr Glu Met Leu Phe Gly Phe Thr Pro Phe Lys Gly Asp Asn
        35                  40                  45

Thr Asn Lys Thr Phe Ser Asn Val Leu Lys Asn Glu Val Ser Phe Pro
    50                  55                  60

Asn Asn Asn Glu Val Ser Arg Ser Cys Lys Asp Leu Ile Arg Lys Leu
65                  70                  75                  80

<210> SEQ ID NO 47
<211> LENGTH: 80
<212> TYPE: PRT
<213> ORGANISM: Vanderwaltozyma polyspora

<400> SEQUENCE: 47

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Ile Tyr Glu Met Leu Phe Gly Phe Thr Pro Phe Lys Gly Asp Asn
        35                  40                  45

Thr Asn Glu Thr Phe Cys Asn Val Leu Lys Asn Asp Val Asn Phe Pro
    50                  55                  60

Asn Asn Asn Glu Ile Ser Arg Thr Cys Lys Asp Leu Ile Lys Lys Leu
65                  70                  75                  80

<210> SEQ ID NO 48
<211> LENGTH: 80
<212> TYPE: PRT
<213> ORGANISM: Zygosaccharomyces rouxii

<400> SEQUENCE: 48

Thr Asn Ser Phe Val Gly Thr Glu Glu Tyr Ile Ala Pro Glu Val Ile
1               5                   10                  15

Arg Gly Asn Gly His Thr Ala Ala Val Asp Trp Trp Thr Leu Gly Ile
            20                  25                  30

Leu Ile Tyr Glu Met Leu Phe Gly Ile Thr Pro Phe Lys Ala Ser Asn

```
                    35                  40                  45
Thr Asn Glu Thr Phe Cys Asn Ile Leu Lys Asn Glu Val Thr Phe Pro
         50                  55                  60

Asn Asn Asn Asp Ile Gly Arg Ser Cys Lys Asp Leu Ile Lys Lys Leu
 65                  70                  75                  80

<210> SEQ ID NO 49
<211> LENGTH: 1320
<212> TYPE: DNA
<213> ORGANISM: Unknown
<220> FEATURE:
<223> OTHER INFORMATION: Obtained from Intestinal Protist of
      Reticulitermes speratus
<220> FEATURE:
<221> NAME/KEY: CDS
<222> LOCATION: (1)..(1320)

<400> SEQUENCE: 49 atg tct caa att ttt aag gat atc cca gtt att aaa tat gaa ggt cca    48
Met Ser Gln Ile Phe Lys Asp Ile Pro Val Ile Lys Tyr Glu Gly Pro
  1               5                  10                  15 gct tcc aag aat cct ttg agt ttc aaa tac tac gat gca aac aag gtt    96
Ala Ser Lys Asn Pro Leu Ser Phe Lys Tyr Tyr Asp Ala Asn Lys Val
                 20                  25                  30 att gat ggt aaa cca atg aag gaa cat ttg aga tac gca atg gct tgg   144
Ile Asp Gly Lys Pro Met Lys Glu His Leu Arg Tyr Ala Met Ala Trp
             35                  40                  45 tgg cat aat ttg tgt gct acc ggt caa gat atg ttt ggt cct ggt act   192
Trp His Asn Leu Cys Ala Thr Gly Gln Asp Met Phe Gly Pro Gly Thr
         50                  55                  60 gca gat aaa tcc ttc ggt agt aag aca gtt ggt acc atg gaa cat gca   240
Ala Asp Lys Ser Phe Gly Ser Lys Thr Val Gly Thr Met Glu His Ala
 65                  70                  75                  80 cat gct aaa gtt gat gct ggt ttt gaa ttc atg tcc aag ttg ggt gtt   288
His Ala Lys Val Asp Ala Gly Phe Glu Phe Met Ser Lys Leu Gly Val
                 85                  90                  95 gaa tac ttc tgt ttc cat gat gct gat ttg gtt cca gaa gca gat act   336
Glu Tyr Phe Cys Phe His Asp Ala Asp Leu Val Pro Glu Ala Asp Thr
            100                 105                 110 ttg agt gaa aca aac aaa aga ttg gat gaa atc gct gaa cat atc gtt   384
Leu Ser Glu Thr Asn Lys Arg Leu Asp Glu Ile Ala Glu His Ile Val
            115                 120                 125 gct aag caa aag gca act ggt att aaa tgt ttg tgg ggt aca gca aat   432
Ala Lys Gln Lys Ala Thr Gly Ile Lys Cys Leu Trp Gly Thr Ala Asn
        130                 135                 140 ttg ttt tct aac cct aga ttc tta aat ggt tct ggt tct tca aac tca   480
Leu Phe Ser Asn Pro Arg Phe Leu Asn Gly Ser Gly Ser Ser Asn Ser
145                 150                 155                 160 gct gat gtt tat gca tac gct gca gct caa att aaa aag gct ttg gat   528
Ala Asp Val Tyr Ala Tyr Ala Ala Ala Gln Ile Lys Lys Ala Leu Asp
                165                 170                 175 ttg act gtt aaa ttt ggt ggt gtt ggt tat gtt ttc tgg ggt ggt aga   576
Leu Thr Val Lys Phe Gly Gly Val Gly Tyr Val Phe Trp Gly Gly Arg
            180                 185                 190 gaa ggt tac gaa acc ttg ttg aac act gat gtt aag ttc gaa caa gaa   624
Glu Gly Tyr Glu Thr Leu Leu Asn Thr Asp Val Lys Phe Glu Gln Glu
            195                 200                 205 aac atc gct aac ttg atg cat ttg gca gtt act tac ggt aga tca atc   672
Asn Ile Ala Asn Leu Met His Leu Ala Val Thr Tyr Gly Arg Ser Ile
        210                 215                 220 ggt ttt aaa ggt gac ttc tac att gaa cca aaa cct aag gaa cca aca   720
```

```
Gly Phe Lys Gly Asp Phe Tyr Ile Glu Pro Lys Pro Lys Glu Pro Thr
225                 230                 235                 240 aag cat caa tat gat ttt gat gca gct act aca att ggt ttc att aga      768
Lys His Gln Tyr Asp Phe Asp Ala Ala Thr Thr Ile Gly Phe Ile Arg
                245                 250                 255 caa tac ggt ttg gaa aag gat ttc aag ttg aac atc gaa gca aac cat      816
Gln Tyr Gly Leu Glu Lys Asp Phe Lys Leu Asn Ile Glu Ala Asn His
            260                 265                 270 gct aca tta gca ggt cat acc ttc caa cat gat ttg aga atc tct gct      864
Ala Thr Leu Ala Gly His Thr Phe Gln His Asp Leu Arg Ile Ser Ala
        275                 280                 285 att aat ggc atg tta ggt tca gtt gat gca aac aca ggt gac cca ttg      912
Ile Asn Gly Met Leu Gly Ser Val Asp Ala Asn Thr Gly Asp Pro Leu
    290                 295                 300 tta ggt tgg gat acc gat gaa ttt cct tat tcc gtt tac gat acc act      960
Leu Gly Trp Asp Thr Asp Glu Phe Pro Tyr Ser Val Tyr Asp Thr Thr
305                 310                 315                 320 ttg gct atg tac gaa att att aag gca ggt ggt ttg acc ggt ggt ttg     1008
Leu Ala Met Tyr Glu Ile Ile Lys Ala Gly Gly Leu Thr Gly Gly Leu
                325                 330                 335 aat ttt gat tcc aag gtt aga aga cca agt tac aca cat gaa gat ttg     1056
Asn Phe Asp Ser Lys Val Arg Arg Pro Ser Tyr Thr His Glu Asp Leu
            340                 345                 350 ttt tac ggt ttc att ttg ggt atg gat tct ttc gct ttg ggt ttg att     1104
Phe Tyr Gly Phe Ile Leu Gly Met Asp Ser Phe Ala Leu Gly Leu Ile
        355                 360                 365 aaa gca aag gct ttg att gca gat ggt aga ttg gat tca ttc gtt aag     1152
Lys Ala Lys Ala Leu Ile Ala Asp Gly Arg Leu Asp Ser Phe Val Lys
    370                 375                 380 gat aga tac gct tct tac ggt tca ggt att ggt gct aag att aga gat     1200
Asp Arg Tyr Ala Ser Tyr Gly Ser Gly Ile Gly Ala Lys Ile Arg Asp
385                 390                 395                 400 cat tct gca act ttg gaa gaa tta gca gct tat gca tta gct aaa gat     1248
His Ser Ala Thr Leu Glu Glu Leu Ala Ala Tyr Ala Leu Ala Lys Asp
                405                 410                 415 aca gtt gct ttg cct ggt tcc ggt aga caa gaa tac tta gaa agt att     1296
Thr Val Ala Leu Pro Gly Ser Gly Arg Gln Glu Tyr Leu Glu Ser Ile
            420                 425                 430 att aac caa att ttg ttt caa taa                                      1320
Ile Asn Gln Ile Leu Phe Gln
        435

<210> SEQ ID NO 50
<211> LENGTH: 439
<212> TYPE: PRT
<213> ORGANISM: Unknown
<220> FEATURE:
<223> OTHER INFORMATION: Synthetic Construct

<400> SEQUENCE: 50

Met Ser Gln Ile Phe Lys Asp Ile Pro Val Ile Lys Tyr Glu Gly Pro
1               5                   10                  15

Ala Ser Lys Asn Pro Leu Ser Phe Lys Tyr Tyr Asp Ala Asn Lys Val
            20                  25                  30

Ile Asp Gly Lys Pro Met Lys Glu His Leu Arg Tyr Ala Met Ala Trp
        35                  40                  45

Trp His Asn Leu Cys Ala Thr Gly Gln Asp Met Phe Gly Pro Gly Thr
    50                  55                  60

Ala Asp Lys Ser Phe Gly Ser Lys Thr Val Gly Thr Met Glu His Ala
65                  70                  75                  80
```

```
His Ala Lys Val Asp Ala Gly Phe Glu Phe Met Ser Lys Leu Gly Val
                85                  90                  95
Glu Tyr Phe Cys Phe His Asp Ala Asp Leu Val Pro Glu Ala Asp Thr
            100                 105                 110
Leu Ser Glu Thr Asn Lys Arg Leu Asp Glu Ile Ala Glu His Ile Val
        115                 120                 125
Ala Lys Gln Lys Ala Thr Gly Ile Lys Cys Leu Trp Gly Thr Ala Asn
130                 135                 140
Leu Phe Ser Asn Pro Arg Phe Leu Asn Gly Ser Gly Ser Ser Asn Ser
145                 150                 155                 160
Ala Asp Val Tyr Ala Tyr Ala Ala Gln Ile Lys Lys Ala Leu Asp
                165                 170                 175
Leu Thr Val Lys Phe Gly Gly Val Gly Tyr Val Phe Trp Gly Gly Arg
            180                 185                 190
Glu Gly Tyr Glu Thr Leu Leu Asn Thr Asp Val Lys Phe Glu Gln Glu
        195                 200                 205
Asn Ile Ala Asn Leu Met His Leu Ala Val Thr Tyr Gly Arg Ser Ile
210                 215                 220
Gly Phe Lys Gly Asp Phe Tyr Ile Glu Pro Lys Pro Lys Glu Pro Thr
225                 230                 235                 240
Lys His Gln Tyr Asp Phe Asp Ala Ala Thr Thr Ile Gly Phe Ile Arg
                245                 250                 255
Gln Tyr Gly Leu Glu Lys Asp Phe Lys Leu Asn Ile Glu Ala Asn His
            260                 265                 270
Ala Thr Leu Ala Gly His Thr Phe Gln His Asp Leu Arg Ile Ser Ala
        275                 280                 285
Ile Asn Gly Met Leu Gly Ser Val Asp Ala Asn Thr Gly Asp Pro Leu
290                 295                 300
Leu Gly Trp Asp Thr Asp Glu Phe Pro Tyr Ser Val Tyr Asp Thr Thr
305                 310                 315                 320
Leu Ala Met Tyr Glu Ile Ile Lys Ala Gly Gly Leu Thr Gly Gly Leu
                325                 330                 335
Asn Phe Asp Ser Lys Val Arg Arg Pro Ser Tyr Thr His Glu Asp Leu
            340                 345                 350
Phe Tyr Gly Phe Ile Leu Gly Met Asp Ser Phe Ala Leu Gly Leu Ile
        355                 360                 365
Lys Ala Lys Ala Leu Ile Ala Asp Gly Arg Leu Asp Ser Phe Val Lys
370                 375                 380
Asp Arg Tyr Ala Ser Tyr Gly Ser Gly Ile Gly Ala Lys Ile Arg Asp
385                 390                 395                 400
His Ser Ala Thr Leu Glu Glu Leu Ala Ala Tyr Ala Leu Ala Lys Asp
                405                 410                 415
Thr Val Ala Leu Pro Gly Ser Gly Arg Gln Glu Tyr Leu Glu Ser Ile
            420                 425                 430
Ile Asn Gln Ile Leu Phe Gln
        435

<210> SEQ ID NO 51
<211> LENGTH: 43
<212> TYPE: DNA
<213> ORGANISM: Artificial Sequence
<220> FEATURE:
<223> OTHER INFORMATION: Synthetic DNA

<400> SEQUENCE: 51
```
ctgacttgag cgtcgaagat tacaagcaag tattagtagc ctc                43

<210> SEQ ID NO 52
<211> LENGTH: 43
<212> TYPE: DNA
<213> ORGANISM: Artificial Sequence
<220> FEATURE:
<223> OTHER INFORMATION: Synthetic DNA

<400> SEQUENCE: 52
ctatacagcg gaattcccat ttgaaatggt ttgaaaatga att                43

<210> SEQ ID NO 53
<211> LENGTH: 43
<212> TYPE: DNA
<213> ORGANISM: Artificial Sequence
<220> FEATURE:
<223> OTHER INFORMATION: Synthetic DNA

<400> SEQUENCE: 53
ctgacttgag cgtcgccatc ttcgatccag gagctcaccg atg                43

<210> SEQ ID NO 54
<211> LENGTH: 45
<212> TYPE: DNA
<213> ORGANISM: Artificial Sequence
<220> FEATURE:
<223> OTHER INFORMATION: Synthetic DNA

<400> SEQUENCE: 54
ctatacagcg gaattgccgg tttcctggat ttttgagcat tttgc              45

<210> SEQ ID NO 55
<211> LENGTH: 43
<212> TYPE: DNA
<213> ORGANISM: Artificial Sequence
<220> FEATURE:
<223> OTHER INFORMATION: Synthetic DNA

<400> SEQUENCE: 55
ctgacttgag cgtcggtgac ttgttcaatt tctgtaccct ttg                43

<210> SEQ ID NO 56
<211> LENGTH: 43
<212> TYPE: DNA
<213> ORGANISM: Artificial Sequence
<220> FEATURE:
<223> OTHER INFORMATION: Synthetic DNA

<400> SEQUENCE: 56
ctatacagcg gaattgatat ttggtctttg ggttgtacgt tct                43

<210> SEQ ID NO 57
<211> LENGTH: 43
<212> TYPE: DNA
<213> ORGANISM: Artificial Sequence
<220> FEATURE:
<223> OTHER INFORMATION: Synthetic DNA

<400> SEQUENCE: 57
ctgacttgag cgtcgtgccc tcctaatttt ttttttttt agt                 43

<210> SEQ ID NO 58
<211> LENGTH: 43
<212> TYPE: DNA

```
<213> ORGANISM: Artificial Sequence
<220> FEATURE:
<223> OTHER INFORMATION: Synthetic DNA

<400> SEQUENCE: 58
ctatacagcg gaattataat cctaggaatg taaaacaaag taa                              43

<210> SEQ ID NO 59
<211> LENGTH: 43
<212> TYPE: DNA
<213> ORGANISM: Artificial Sequence
<220> FEATURE:
<223> OTHER INFORMATION: Synthetic DNA

<400> SEQUENCE: 59
ctgacttgag cgtcgtgagc acccttactt aataaaagag ttg                              43

<210> SEQ ID NO 60
<211> LENGTH: 43
<212> TYPE: DNA
<213> ORGANISM: Artificial Sequence
<220> FEATURE:
<223> OTHER INFORMATION: Synthetic DNA

<400> SEQUENCE: 60
ctatacagcg gaattgactt cctttcatca aaaatgaagg atc                              43

<210> SEQ ID NO 61
<211> LENGTH: 43
<212> TYPE: DNA
<213> ORGANISM: Artificial Sequence
<220> FEATURE:
<223> OTHER INFORMATION: Synthetic DNA

<400> SEQUENCE: 61
ctgacttgag cgtcggacta ttttaattac gttggtgtca ttg                              43

<210> SEQ ID NO 62
<211> LENGTH: 43
<212> TYPE: DNA
<213> ORGANISM: Artificial Sequence
<220> FEATURE:
<223> OTHER INFORMATION: Synthetic DNA

<400> SEQUENCE: 62
ctatacagcg gaattagatt cgttttcttt ttctcgttgt tca                              43

<210> SEQ ID NO 63
<211> LENGTH: 30
<212> TYPE: DNA
<213> ORGANISM: Artificial Sequence
<220> FEATURE:
<223> OTHER INFORMATION: Synthetic DNA

<400> SEQUENCE: 63
ataccagtga caagagagca ggttgaacac                                             30

<210> SEQ ID NO 64
<211> LENGTH: 29
<212> TYPE: DNA
<213> ORGANISM: Artificial Sequence
<220> FEATURE:
<223> OTHER INFORMATION: Synthetic DNA

<400> SEQUENCE: 64
gtctataaaa gttgtttatt cttgtgagg                                              29
```

<210> SEQ ID NO 65
<211> LENGTH: 30
<212> TYPE: DNA
<213> ORGANISM: Artificial Sequence
<220> FEATURE:
<223> OTHER INFORMATION: Synthetic DNA

<400> SEQUENCE: 65
cgaccacgag caagaacacg aacacgattc        30

<210> SEQ ID NO 66
<211> LENGTH: 29
<212> TYPE: DNA
<213> ORGANISM: Artificial Sequence
<220> FEATURE:
<223> OTHER INFORMATION: Synthetic DNA

<400> SEQUENCE: 66
cgctcttatt catgttcgtg atggtgtcc         29

<210> SEQ ID NO 67
<211> LENGTH: 30
<212> TYPE: DNA
<213> ORGANISM: Artificial Sequence
<220> FEATURE:
<223> OTHER INFORMATION: Synthetic DNA

<400> SEQUENCE: 67
ctacactaaa gaagaaaaag aagactaaaa        30

<210> SEQ ID NO 68
<211> LENGTH: 30
<212> TYPE: DNA
<213> ORGANISM: Artificial Sequence
<220> FEATURE:
<223> OTHER INFORMATION: Synthetic DNA

<400> SEQUENCE: 68
ggtcgaatcc taactaagca gctaaatcgg        30

<210> SEQ ID NO 69
<211> LENGTH: 30
<212> TYPE: DNA
<213> ORGANISM: Artificial Sequence
<220> FEATURE:
<223> OTHER INFORMATION: Synthetic DNA

<400> SEQUENCE: 69
taagcaataa tcgcgataat gttaatggta        30

<210> SEQ ID NO 70
<211> LENGTH: 29
<212> TYPE: DNA
<213> ORGANISM: Artificial Sequence
<220> FEATURE:
<223> OTHER INFORMATION: Synthetic DNA

<400> SEQUENCE: 70
gtgatggtta ggtgaagtta tgctgcatg         29

<210> SEQ ID NO 71
<211> LENGTH: 30
<212> TYPE: DNA
<213> ORGANISM: Artificial Sequence
<220> FEATURE:

```
<223> OTHER INFORMATION: Synthetic DNA

<400> SEQUENCE: 71
aatataaaaa gcattatagg atcatcgtac                                              30

<210> SEQ ID NO 72
<211> LENGTH: 30
<212> TYPE: DNA
<213> ORGANISM: Artificial Sequence
<220> FEATURE:
<223> OTHER INFORMATION: Synthetic DNA

<400> SEQUENCE: 72
gttttgttcc aattacgaag atccaacagg                                              30

<210> SEQ ID NO 73
<211> LENGTH: 30
<212> TYPE: DNA
<213> ORGANISM: Artificial Sequence
<220> FEATURE:
<223> OTHER INFORMATION: Synthetic DNA

<400> SEQUENCE: 73
tacattaaaa ctaaatactg gtgcctccat                                              30

<210> SEQ ID NO 74
<211> LENGTH: 30
<212> TYPE: DNA
<213> ORGANISM: Artificial Sequence
<220> FEATURE:
<223> OTHER INFORMATION: Synthetic DNA

<400> SEQUENCE: 74
gcagaagaat tcttttacgt agcaggcatg                                              30
```